US008944997B2

(12) United States Patent
Fernandez et al.

(10) Patent No.: US 8,944,997 B2
(45) Date of Patent: Feb. 3, 2015

(54) MEDICAL DEVICES AND METHODS

(75) Inventors: Raul Fernandez, Arlington, TX (US); Daniel J. Scott, Dallas, TX (US); Shou Jiang Tang, Ridgeland, MS (US); Jeffrey A. Cadeddu, Dallas, TX (US); Richard A. Bergs, Grand Prairie, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 290 days.

(21) Appl. No.: 13/144,668

(22) PCT Filed: Jan. 16, 2010

(86) PCT No.: PCT/US2010/021292
§ 371 (c)(1),
(2), (4) Date: Oct. 4, 2011

(87) PCT Pub. No.: WO2010/083480
PCT Pub. Date: Jul. 22, 2010

(65) Prior Publication Data
US 2012/0035416 A1    Feb. 9, 2012

Related U.S. Application Data

(60) Provisional application No. 61/145,463, filed on Jan. 16, 2009.

(51) Int. Cl.
*A61B 1/04* (2006.01)
*A61B 1/06* (2006.01)
(Continued)

(52) U.S. Cl.
CPC .............. *A61B 1/05* (2013.01); *A61B 1/00179* (2013.01); *A61B 1/00149* (2013.01);
(Continued)

(58) Field of Classification Search
CPC ..................... A61B 17/00234; A61B 17/3421; A61B 19/2203; A61B 19/5212; A61B 1/05; A61B 1/313; A61B 1/3132; A61B 2017/00871; A61B 2017/00876; A61B 2017/3449; A61B 2019/2226; A61B 2019/2253; A61B 2019/5206
USPC .......................... 600/102, 104, 127, 129, 157
See application file for complete search history.

(56) References Cited

U.S. PATENT DOCUMENTS

| 4,802,461 A | 2/1989 | Cho ................................. 128/7 |
| 5,313,306 A | 5/1994 | Kuban et al. .................... 348/65 |

(Continued)

OTHER PUBLICATIONS

International Search Report and Written Opinion in PCT/US2010/021292 issued Aug. 27, 2010.
(Continued)

*Primary Examiner* — John P Leubecker
*Assistant Examiner* — Arnaldo Torres Diaz
(74) *Attorney, Agent, or Firm* — Fulbright & Jaworski LLP

(57) ABSTRACT

The present invention relates generally to medical devices and methods. The present medical devices comprises a platform comprising a magnetically-attractive material, and a camera coupled to the platform and configured to be moved in at least three degrees of freedom relative to the platform, where the camera's movement in each respective degree of freedom is controlled by a separate actuator coupled to the platform. The medical devices further comprise a housing disposed around at least a portion of the camera, the housing being at least partially transparent, and a wiper arm configured to move relative to the housing. Some embodiments of the present multi-degree-of-freedom cameras for a medical procedure, comprises a platform comprising a magnetically-attractive material, an apparatus to moving the platform within a body cavity of a patient when the apparatus is outside the body cavity, the apparatus comprising a magnetic assembly, and a camera coupled to the platform, and configured to be moved in at least three degrees of freedom relative to the platform, where the camera's movement in each respective degree of freedom is controlled by a separate actuator coupled to the platform.

12 Claims, 25 Drawing Sheets

(51) Int. Cl.
*A61B 1/05* (2006.01)
*A61B 1/00* (2006.01)
*A61B 17/34* (2006.01)
*A61B 19/00* (2006.01)
*A61B 1/313* (2006.01)
*A61B 17/00* (2006.01)

(52) U.S. Cl.
CPC ........ *A61B 17/3421* (2013.01); *A61B 19/2203* (2013.01); *A61B 1/00163* (2013.01); *A61B 1/00147* (2013.01); *A61B 1/313* (2013.01); *A61B 17/00234* (2013.01); *A61B 19/5212* (2013.01); *A61B 2017/00871* (2013.01); *A61B 2017/00876* (2013.01); *A61B 2017/3449* (2013.01); *A61B 2019/2226* (2013.01); *A61B 2019/2253* (2013.01); *A61B 2019/5206* (2013.01)
USPC .......... 600/109; 600/112; 600/129; 600/160; 600/164; 600/175

(56) References Cited

U.S. PATENT DOCUMENTS

| | | | | |
|---|---|---|---|---|
| 5,604,531 | A | 2/1997 | Iddan et al. | 348/76 |
| 5,810,718 | A | 9/1998 | Akiba et al. | 600/153 |
| 5,957,849 | A | 9/1999 | Munro | 600/459 |
| 6,083,151 | A | 7/2000 | Renner et al. | 600/114 |
| 6,221,007 | B1 | 4/2001 | Green | 600/160 |
| 7,044,937 | B1 | 5/2006 | Kirwan et al. | 604/264 |
| 8,460,180 | B1* | 6/2013 | Zarate et al. | 600/127 |
| 2002/0055668 | A1 | 5/2002 | Pauker | 600/140 |
| 2003/0009130 | A1 | 1/2003 | Stecker et al. | 604/104 |
| 2003/0114731 | A1 | 6/2003 | Cadeddu et al. | 600/114 |
| 2003/0208187 | A1* | 11/2003 | Layer | 606/1 |
| 2003/0212417 | A1 | 11/2003 | Rudnick et al. | 606/139 |
| 2004/0050394 | A1 | 3/2004 | Jin | 128/899 |
| 2004/0193007 | A1 | 9/2004 | Martone et al. | 600/104 |
| 2004/0249367 | A1 | 12/2004 | Saadat et al. | 606/1 |
| 2004/0267254 | A1 | 12/2004 | Manzo et al. | 606/41 |
| 2005/0085691 | A1 | 4/2005 | Nakao | 600/128 |
| 2005/0096502 | A1 | 5/2005 | Khalili | 600/106 |
| 2005/0165449 | A1 | 7/2005 | Cadeddu et al. | 606/1 |
| 2005/0234294 | A1 | 10/2005 | Saadat et al. | 600/104 |
| 2006/0195070 | A1 | 8/2006 | Hagn | 606/1 |
| 2007/0182842 | A1 | 8/2007 | Sonnenschein et al. | 348/340 |
| 2007/0249932 | A1 | 10/2007 | Shahinian | 600/421 |
| 2007/0255273 | A1 | 11/2007 | Fernandez et al. | 606/41 |
| 2007/0276424 | A1 | 11/2007 | Mikkaichi et al. | 606/185 |
| 2008/0004634 | A1 | 1/2008 | Farritor et al. | 606/130 |
| 2008/0058835 | A1 | 3/2008 | Farritor et al. | 606/130 |
| 2008/0058989 | A1* | 3/2008 | Oleynikov et al. | 700/259 |
| 2008/0065098 | A1 | 3/2008 | Larkin | 606/130 |
| 2008/0065102 | A1 | 3/2008 | Cooper | 606/130 |
| 2008/0065108 | A1 | 3/2008 | Diolaiti | 700/247 |
| 2008/0065110 | A1 | 3/2008 | Duval et al. | 600/104 |
| 2008/0071291 | A1 | 3/2008 | Duval et al. | 606/130 |
| 2008/0208220 | A1 | 8/2008 | Shiono et al. | 606/232 |
| 2008/0215066 | A1* | 9/2008 | Layer | 606/130 |
| 2008/0269779 | A1 | 10/2008 | Cadeddu et al. | 606/130 |
| 2009/0240111 | A1* | 9/2009 | Kessler et al. | 600/155 |
| 2010/0174144 | A1* | 7/2010 | Hsu et al. | 600/122 |
| 2013/0131694 | A1* | 5/2013 | Farritor et al. | 606/130 |
| 2014/0005555 | A1* | 1/2014 | Tesar | 600/476 |
| 2014/0066955 | A1* | 3/2014 | Farritor et al. | 606/130 |

OTHER PUBLICATIONS

Sangtae, et at, *Annals of Surgery.* 245(3): 379-384, 2007.
Abbott, et al. *Proceedings of the 2007 IEEE/RDJ International Conference on Intelligent Robots and Systems.* 410-416, 2007.
International Preliminary Report on Patentability in PCT/US2010/021292 issued Jul. 19, 2011.

* cited by examiner

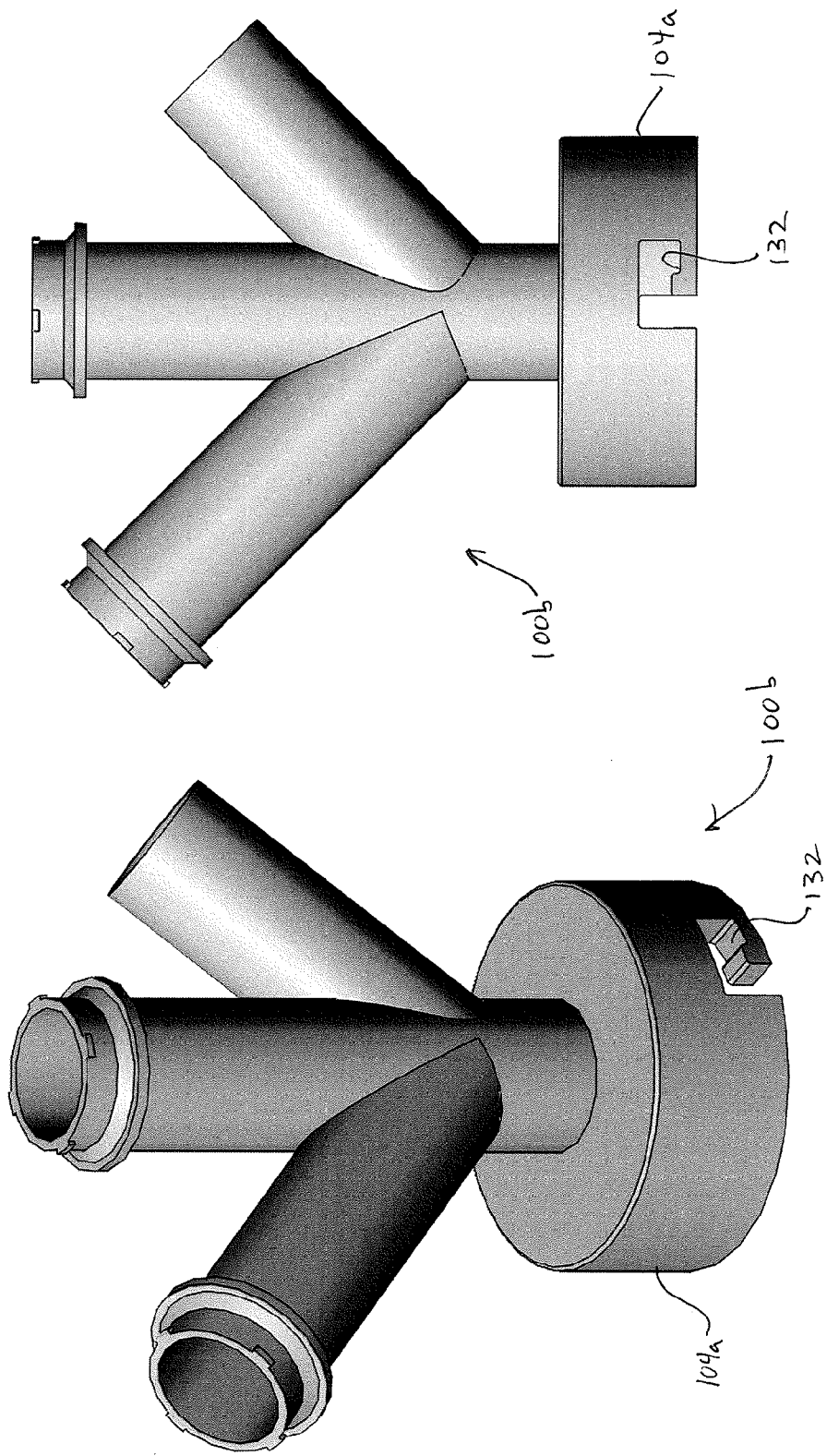

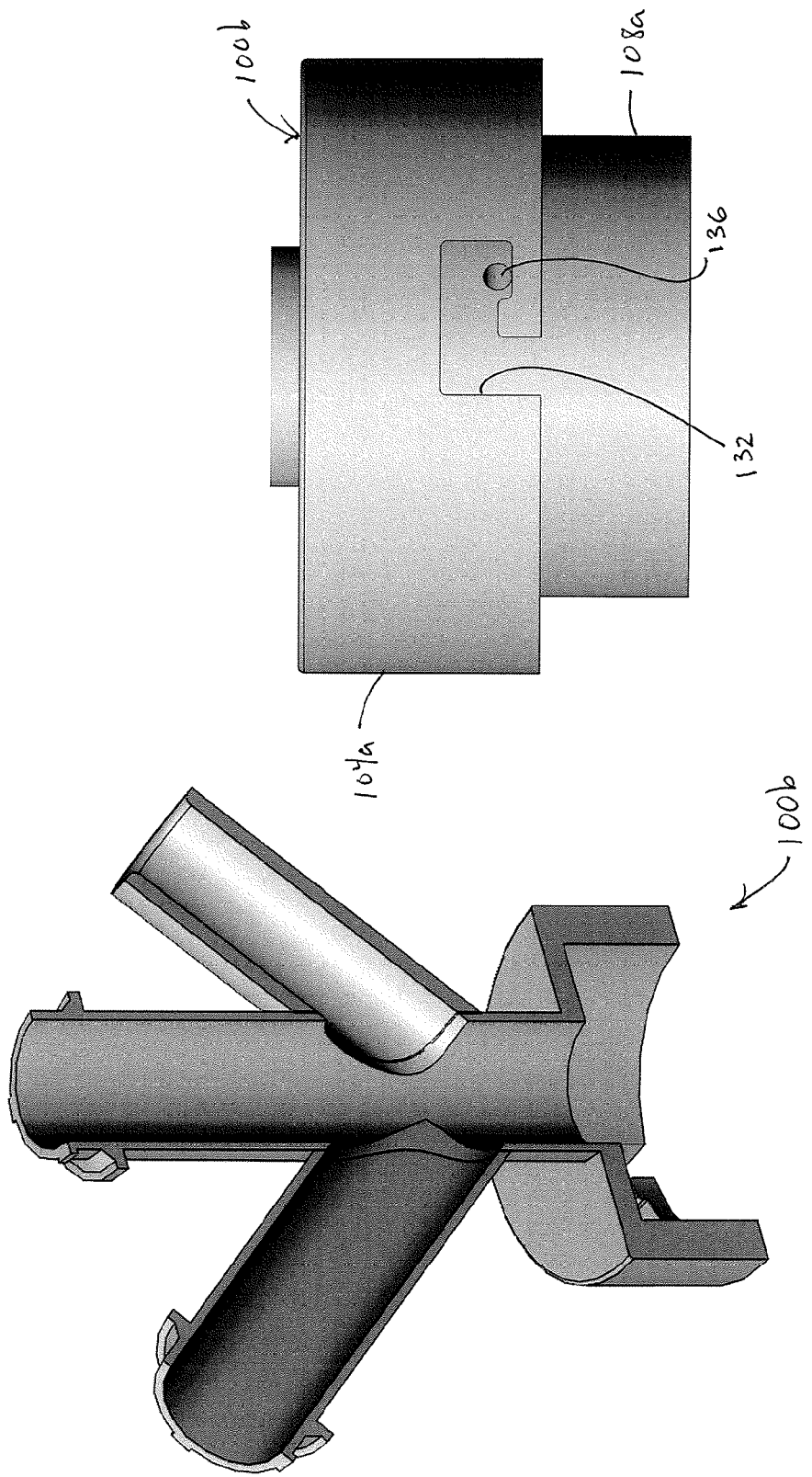

MEDICAL DEVICES AND METHODS

CROSS REFERENCE TO RELATED APPLICATIONS

This application is a national phase application under 35 U.S.C. 371 of International Application No. PCT/US2010/021292, filed Jan. 16, 2010, which claims priority to U.S. Provisional Patent Application Ser. No. 61/145,463, filed on Jan. 16, 2009, the entire contents of both of which are incorporated by reference.

BACKGROUND OF THE INVENTION

1. Field of the Invention

The present invention relates generally to medical devices, apparatuses, systems, and methods, and, more particularly, but not by way of limitation, to medical devices, apparatuses, systems, and methods for performing medical procedures at least partially within a body cavity of a patient.

2. Description of Related Art

For illustration, but without limiting the scope of the invention, the background is described with respect to medical procedures (e.g., surgical procedurals), which can include laparoscopy, transmural surgery, and endoluminal surgery, including, for example, natural orifice transluminal endoscopic surgery (NOTES), single-incision laparoscopic surgery (SILS), and single-port laparoscopy (SLP).

Compared with open surgery, laparoscopy can result in significantly less pain, faster convalescence and less morbidity. NOTES, which can be an even less-invasive surgical approach, may achieve similar results. However, issues such as eye-hand dissociation, a two-dimensional field-of-view, instrumentation with limited degrees of freedom, and demanding dexterity requirements can pose challenges for many laparoscopic and endoscopic procedures. One limitation of laparoscopy can be the fixed working envelope surrounding each trocar. As a result, multiple ports may be used to accommodate changes in position of the instruments or laparoscope, for example, to improve visibility and efficiency. However, the placement of additional working ports may contribute to post-operative pain and increases risks, such as additional bleeding and adjacent organ damage.

The following published patent applications include information that may be useful in understanding the present medical devices, apparatuses, systems, and methods, and each is incorporated by reference in its entirety: (1) U.S. patent application Ser. No. 10/024,636, filed Dec. 14, 2001, and published as Pub. No. US 2003/0114731; (2) U.S. patent application Ser. No. 10/999,396, filed Nov. 30, 2004, and published as Pub. No. US 2005/0165449; (3) U.S. patent application Ser. No. 11/741,731, filed Apr. 28, 2007, and published as Pub. No. US 2007/0255273; (4) U.S. patent application Ser. No. 11/833,729, filed Aug. 3, 2007, and published as Pub. No. US 2007/0276424; and (5) U.S. patent application Ser. No. 11/711,541, filed Feb. 27, 2007, and published as Pub. No. US 2008/0208220.

SUMMARY OF THE INVENTION

Some embodiments of the present medical devices comprise: a platform comprising a magnetically-attractive material; and a camera coupled to the platform and configured to be moved in at least three degrees of freedom relative to the platform, where the camera's movement in each respective degree of freedom is controlled by a separate actuator coupled to the platform. Some embodiments comprise: a housing disposed around at least a portion of the camera, the housing being at least partially transparent. Some embodiments comprise: a wiper arm configured to move relative to the housing. In some embodiments, the wiper arm comprises a resilient wiper blade coupled to the wiper arm, and the medical device is configured such that the wiper blade contacts the housing such that if the housing moves relative to the wiper arm, at least a portion of the wiper blade maintains contact with the housing. In some embodiments, the wiper arm is configured to move relative to the platform. In some embodiments, the housing is coupled in fixed relation to the platform. In some embodiments, the housing is configured to rotate relative to the platform. In some embodiments, the housing is configured to rotate relative to the platform. In some embodiments, the wiper arm is coupled in fixed relation to the platform.

In some embodiments, the platform is configured such that if the platform is disposed in a body cavity of a patient, the platform can be percutaneously coupled to a power source external to the body cavity. In some embodiments, the platform comprises a power source. In some embodiments, the power source comprises a battery.

In some embodiments, the platform comprises a body and a camera arm pivotally coupled to the body, the camera is coupled to the camera arm, and the camera arm is configured to be pivoted between a collapsed position and a deployed position. In some embodiments, the camera arm is pivotally coupled to the platform such that in the collapsed position, the camera is configured to face away from the platform. In some embodiments, the platform comprises a hinge pivotally coupling the body and the camera arm. In some embodiments, the camera is configured to be coupled to an external display through the hinge. In some embodiments, the camera is configured to be coupled to an external display by a wire that extends through the hinge.

In some embodiments, the platform includes a lower surface, and the camera has a lens disposed below the lower surface of the platform. In some embodiments, the platform has two ends and a longitudinal midpoint, and the camera is coupled to the platform such that the camera is nearer the midpoint than either end. In some embodiments, the device is configured such that the camera can be used to view a 360-degree field-of-view around the platform without moving the platform. In some embodiments, substantially all of the housing viewable by the camera is substantially transparent.

In some embodiments, the camera is configured to detect light in the visible spectrum. In some embodiments, the camera is configured to detect light in the infrared (IR) spectrum. In some embodiments, the camera is configured to detect light in all of the visible, IR, and ultraviolet (UV) spectra. In some embodiments, the camera comprises a plurality of cameras configured to detect light in all of the visible, IR, and UV spectra.

Some embodiments of the present multi-degree-of-freedom cameras for a medical procedure, comprise: a platform comprising a magnetically-attractive material; an apparatus for moving the platform within a body cavity of a patient when the apparatus is outside the body cavity, the apparatus comprising a magnetic assembly; and a camera coupled to the platform, and configured to be moved in at least three degrees of freedom relative to the platform, where the camera's movement in each respective degree of freedom is controlled by a separate actuator coupled to the platform.

Some embodiments of the present medical devices comprise: a branched connector having an overtube connection configured to be coupled to an overtube, the branched connector having at least two entry ports that each includes at least one seal structure, one of the seal structures being configured to accept and maintain a seal around a portion of an endoscope, the branched connector being configured to connect to an insuflation device downstream of the seal structure or seal structures for a given entry port for the introduction and maintenance of pneumoperitoneum. In some embodiments, the branched connector includes a straight portion associated with one of the entry ports, and a side branch portion associated with the other entry port. In some embodiments, the branched connector has a Y-shaped configuration. In some embodiments, the branch connector is configured with two connections that each can be used to connect to an insuflation device. In some embodiments, the overtube connector is configured to be adhered to an overtube. In some embodiments, the overtube connector is configured to be threaded onto a correspondingly threaded overtube. In some embodiments, the overtube connection is configured to be press-fit onto an overtube. In some embodiments, the overtube connection includes one of a tab and a corresponding slot, and is configured to be coupled to an overtube having the other of a tab and a corresponding slot by inserting the tab into the corresponding slot and turning the tab relative to the corresponding slot. In some embodiments, the branched connector has more than two entry ports each including at least one seal structure. Some embodiments comprise: an overtube coupled to the overtube connection of the branched connector. In some embodiments, the overtube is rigid.

Some embodiments of the present medical devices comprise: an overtube comprising an overtube wall that defines a main lumen, the overtube also including channels within the wall. None, one or more, or all of the channels may be open to the main lumen. None, one or more, or all of the channels may be closed. In some embodiments, the overtube is rigid. In some embodiments, the overtube comprises a flexible material, and is configured such that at least a portion of the overtube can be made substantially rigid by pressurizing the at least a portion of the overtube. In some embodiments, the overtube has a length, and is configured such that the overtube can be made substantially rigid along its length by pressurizing the at least a portion of the overtube. Some embodiments comprise: any of the present branched connectors coupled to the overtube. In some embodiments, at least one of the channels is configured to permit a tether to extend through the channel. In some embodiments, at least one of the channels is configured to permit an optical fiber to extend through the channel.

Some of the present medical devices comprise: a set of multi-degree-of-freedom arms equipped with interchangeable tips, each arm including at least two joints, each joint associated with an actuator. In some embodiments, the interchangeable tips are configured to be actuatable in one or more degrees of freedom relative to an arm to which the interchangeable tip is coupled. In some embodiments, at least one of the interchangeable tips comprises a camera. In some embodiments, at least one of the interchangeable tips comprises a cautery tool. In some embodiments, at least one of the interchangeable tips comprises a grasper. In some embodiments, the grasper is coupled to an arm configured such that the grasper is actuatable through an angular range of at least 90 degrees in at least one degree of freedom relative to the arm. In some embodiments, the grasper is coupled to an arm configured such that the grasper is actuatable through an angular range of at least 120 degrees in at least one degree of freedom relative to the arm. In some embodiments, at least one of the interchangeable tips comprises a stapler. In some embodiments, at least one of the interchangeable tips comprises a clip applier. Some embodiments comprise: a rigid overtube through which one or more of the arms can be introduced. Some embodiments comprise: a rigid overtube comprising a rigid overtube wall that includes at least two channels, each channel being sized to receive one of the arms. In some embodiments, the set of multi-degree-of-freedom arms comprises three or more multi-degree-of-freedom arms.

Some embodiments of the present methods include manipulating an arm that includes a camera coupled to the arm within a channel in the wall of a tube (e.g., an overtube), where the channel is open or closed to a main lumen within the overtube; and positioning an endoscope in the main lumen of the overtube. In further embodiments, the overtube may be configured with any of the features described in this disclosure, and any of the multi-DOF arms described in this disclosure may be used with the overtube.

Some embodiments of the present methods include pressuring and depressurizing one or more pressurizable sections of a tube (e.g., an overtube) during a NOTES procedure. In further embodiments, the overtube may include multiple channels in a wall that defines a main lumen, and any of the multi-DOF arms described in this disclosure may be used with the overtube.

Some embodiments of the present methods include interchanging a tip coupled to a multi-degree-of-freedom arm with a tip that includes a camera during a NOTES procedure. In further embodiments, the arm may be positioned at least partially in an overtube configured with any of the features described in this disclosure, and any of the multi-DOF arms described in this disclosure may also be used with the overtube.

Any embodiment of any of the present medical devices or systems and methods can consist of or consist essentially of—rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 23-26 depict various views of another embodiment of the present branched connectors configured to be coupled to a surgical overtube.

DESCRIPTION OF ILLUSTRATIVE EMBODIMENTS

Figure 1:
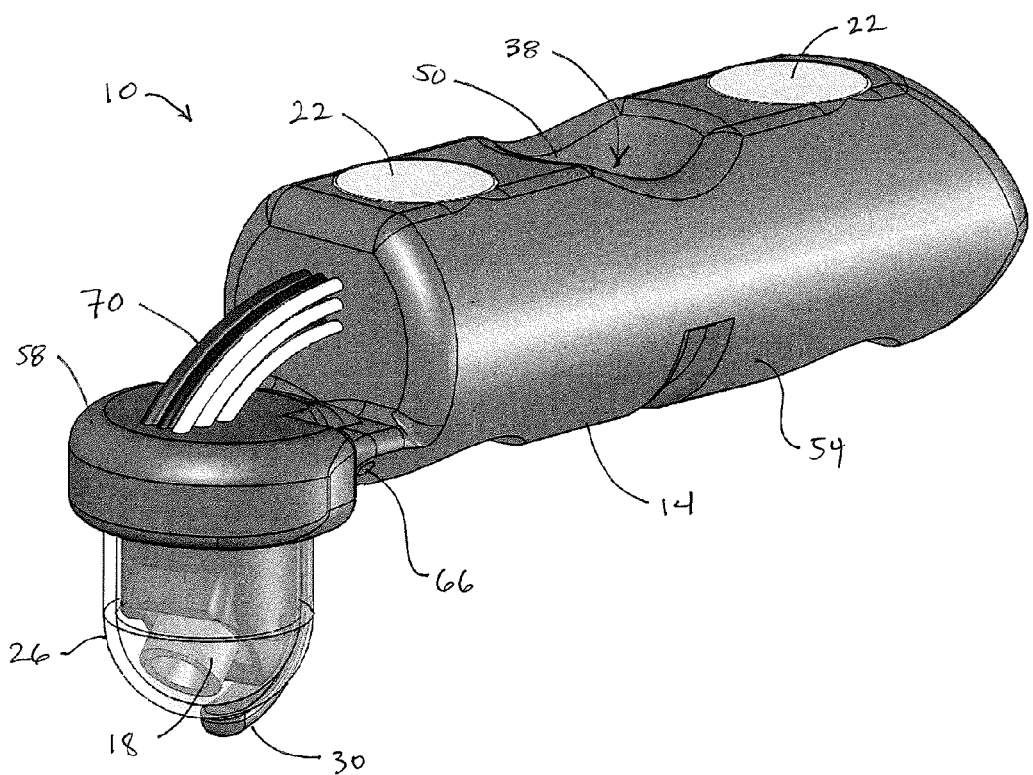
FIGS. 1-4 depict various views of one of the present medical devices comprising a magnetically attractive platform; and multi-degree-of-freedom camera.
Figure 2:
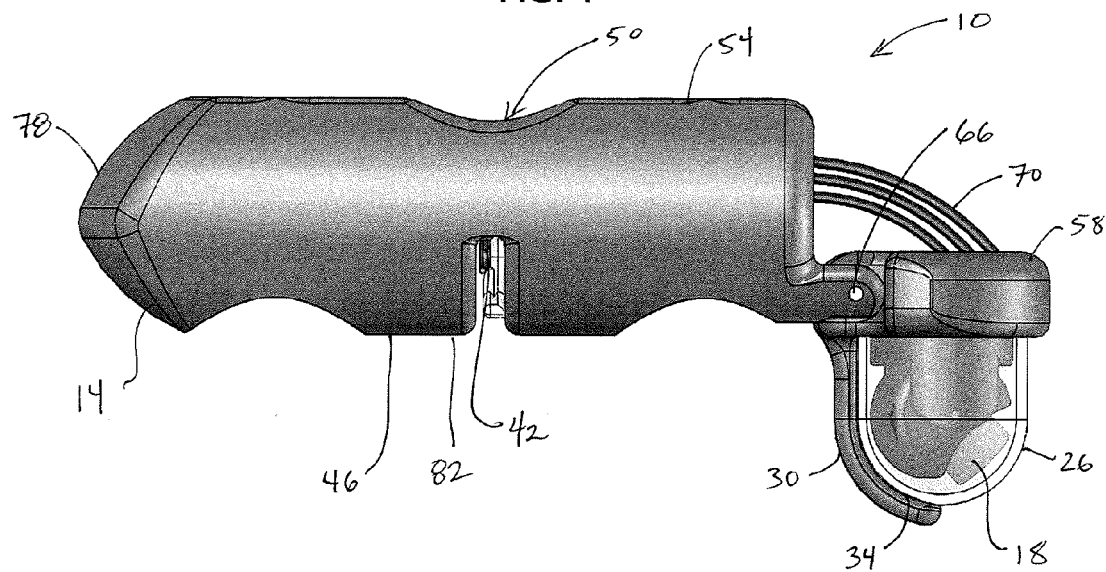
Figure 4:
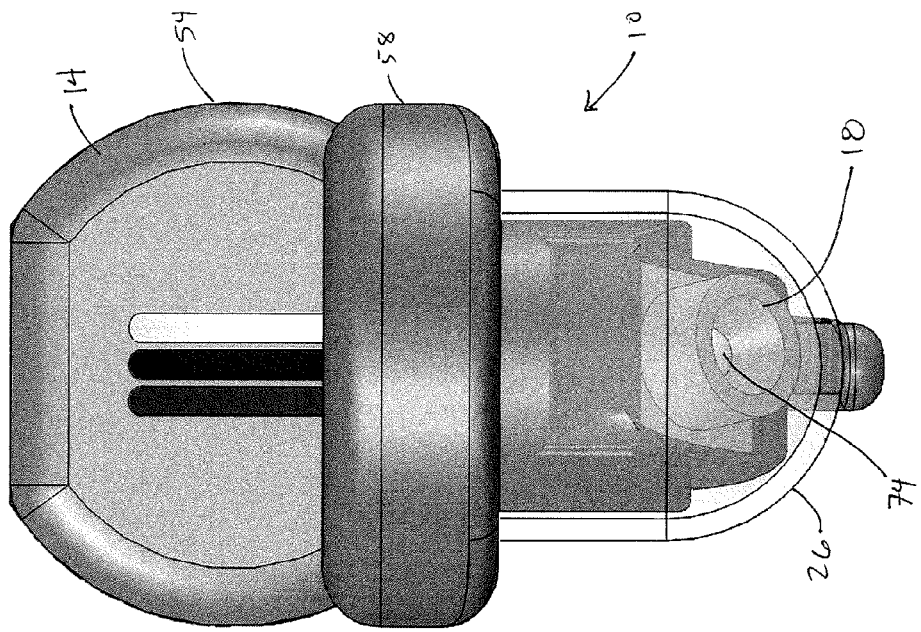
Figure 3:
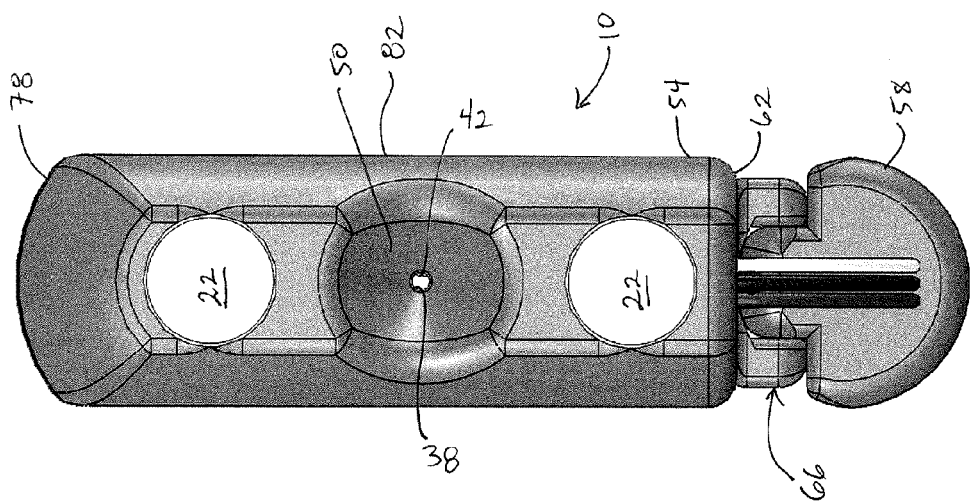
Figure 5:
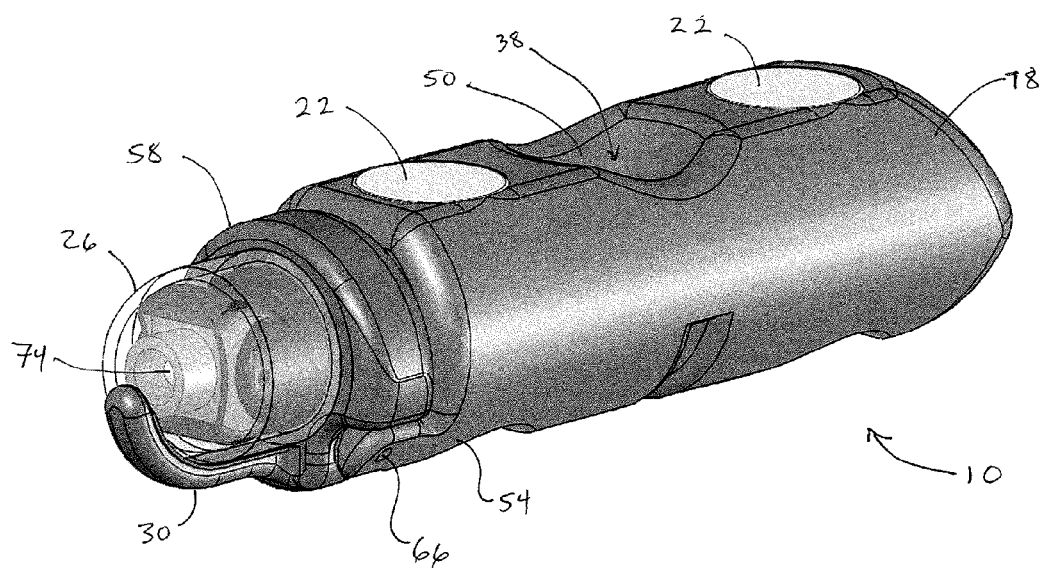
FIGS. 5-8 depict various views of the medical device of FIGS. 1-4 with the camera in a collapsed position.
Figure 6:
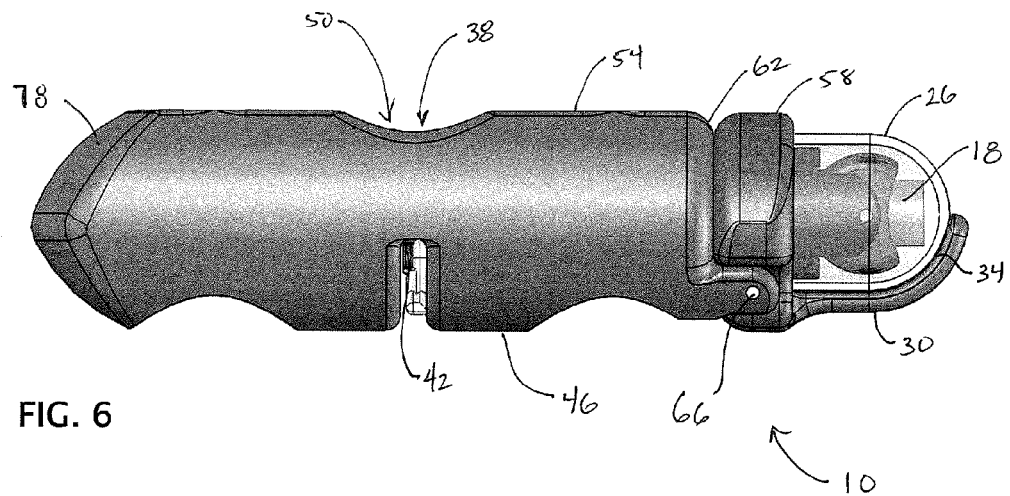
Figure 8:
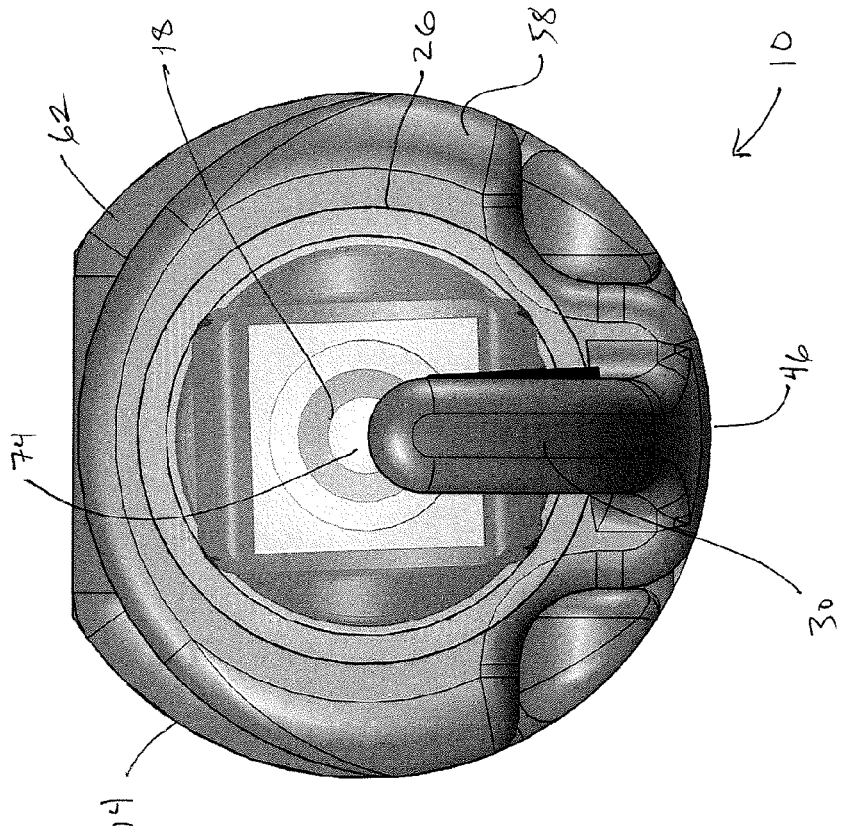
Figure 7:
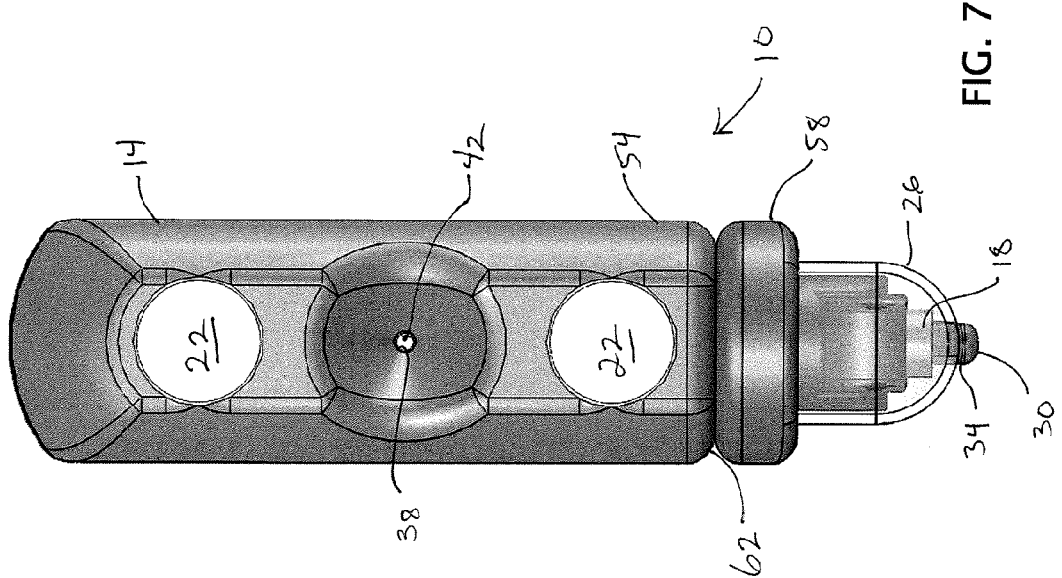
Figure 9:
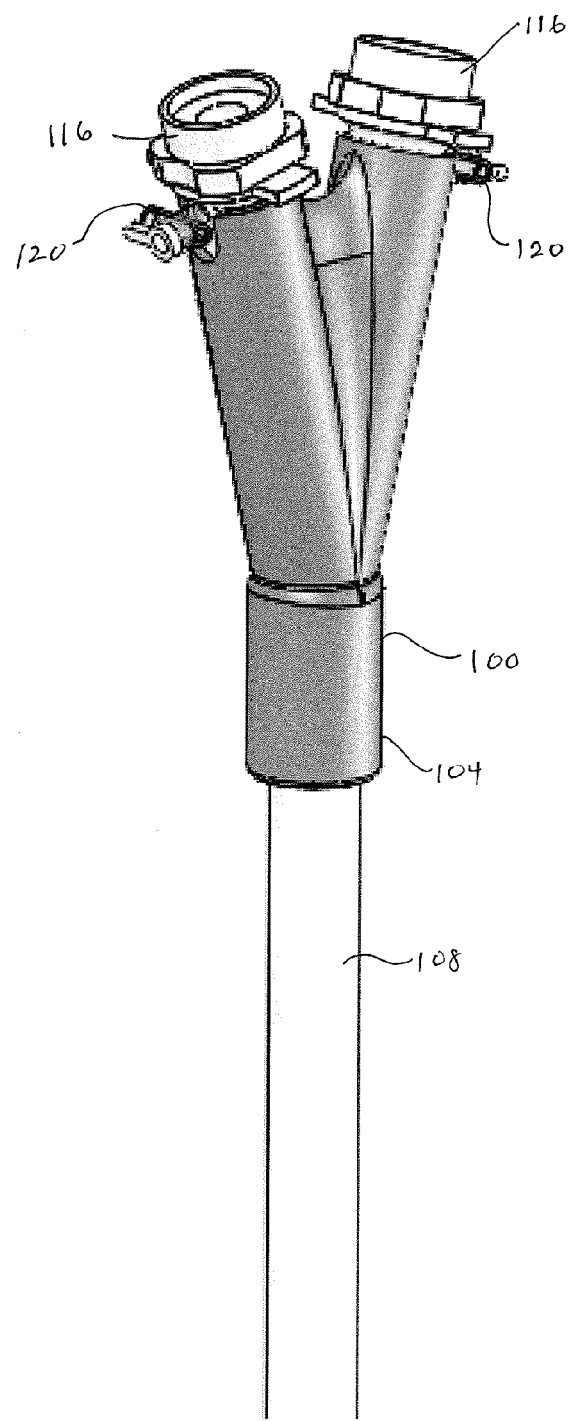
FIGS. 9-16 depict various views of one embodiment of the present branched connectors configured to be coupled to a surgical overtube.
Figure 10:
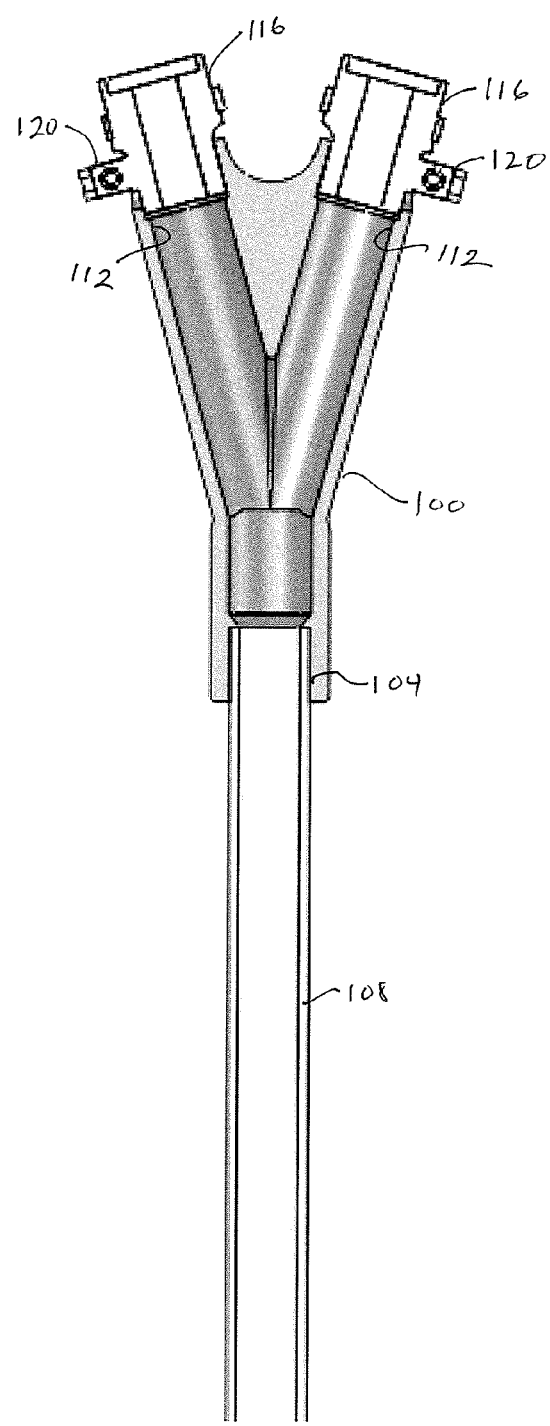
Figure 13:
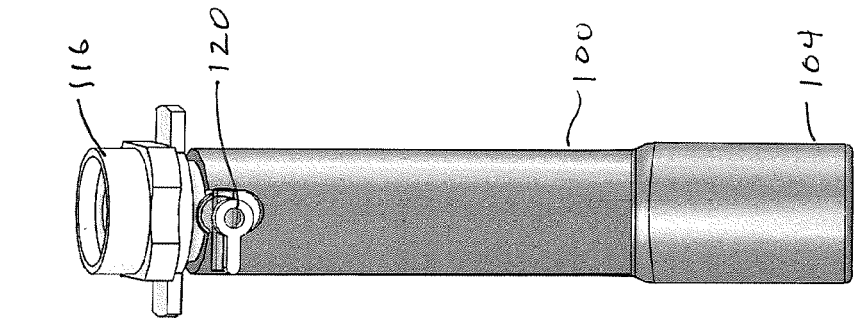
Figure 12:
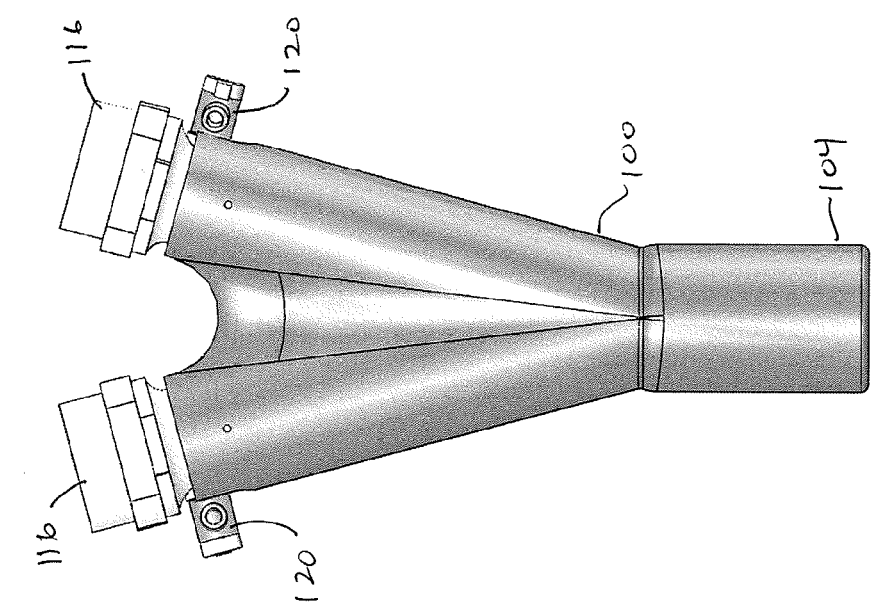
Figure 11:
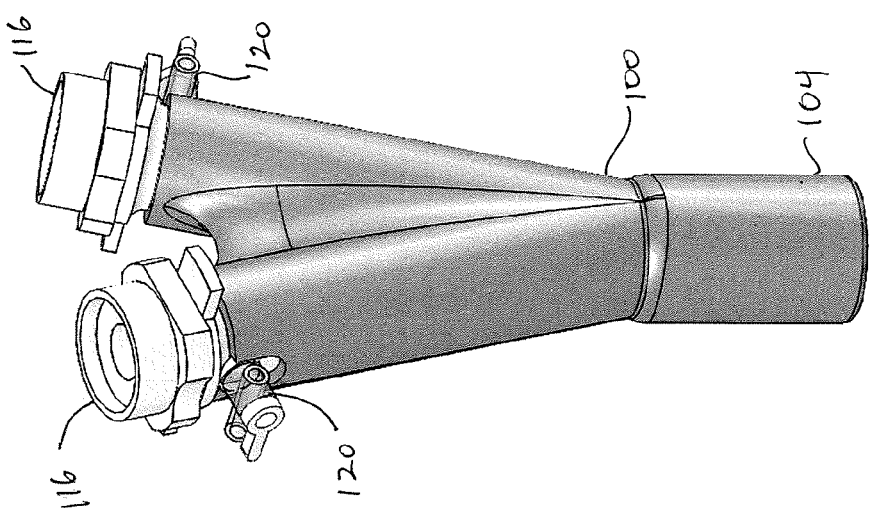
Figure 14:
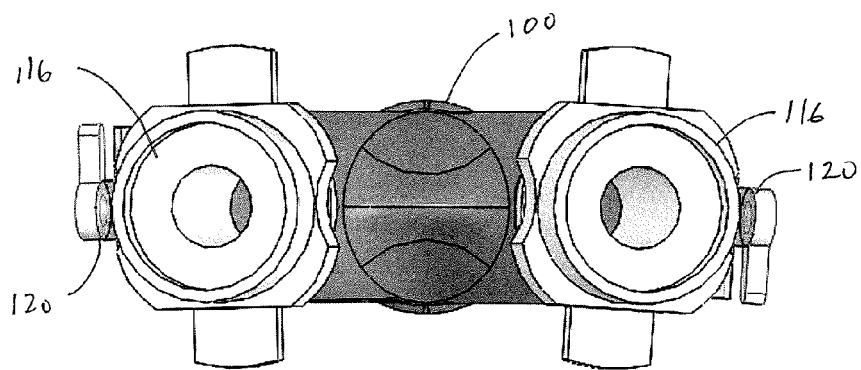
Figures 15, 16:
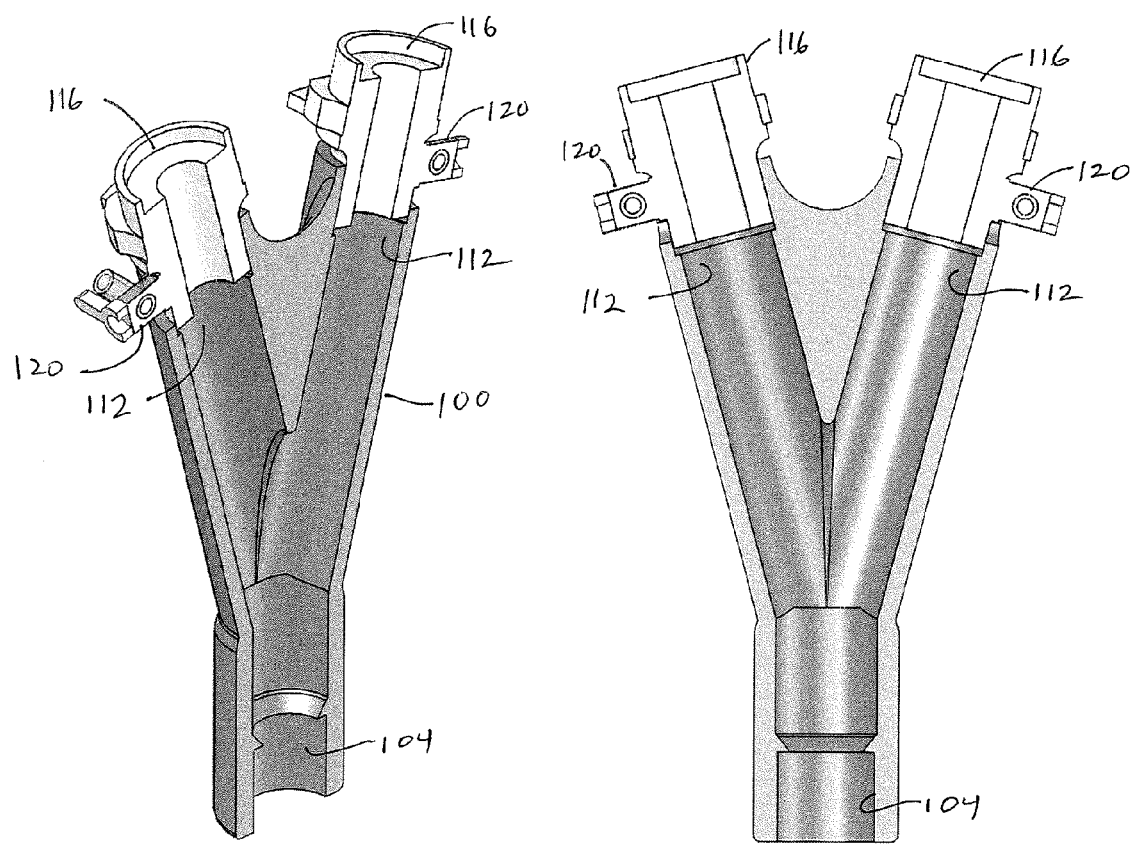
Figure 18:
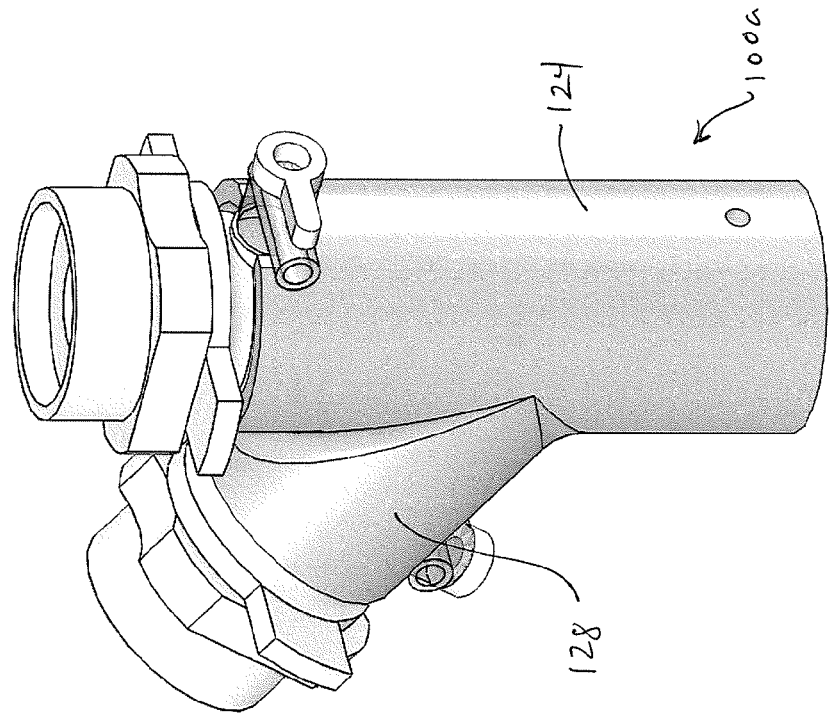
FIGS. 17-22 depict various views of another embodiment of the present branched connectors configured to be coupled to a surgical overtube.
Figure 17:
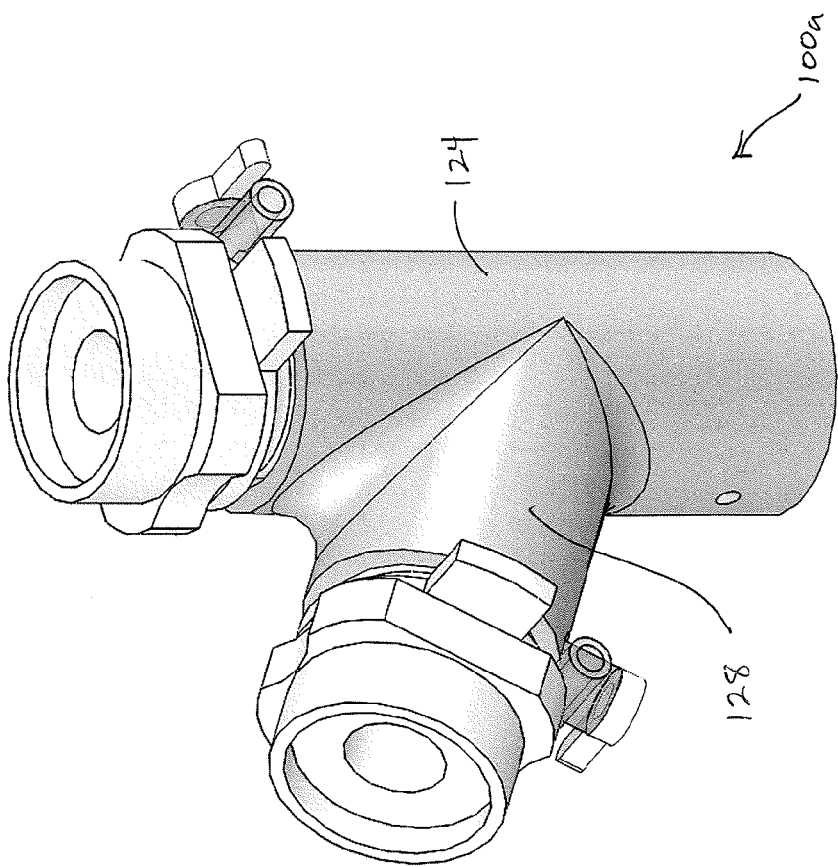
Figure 20:
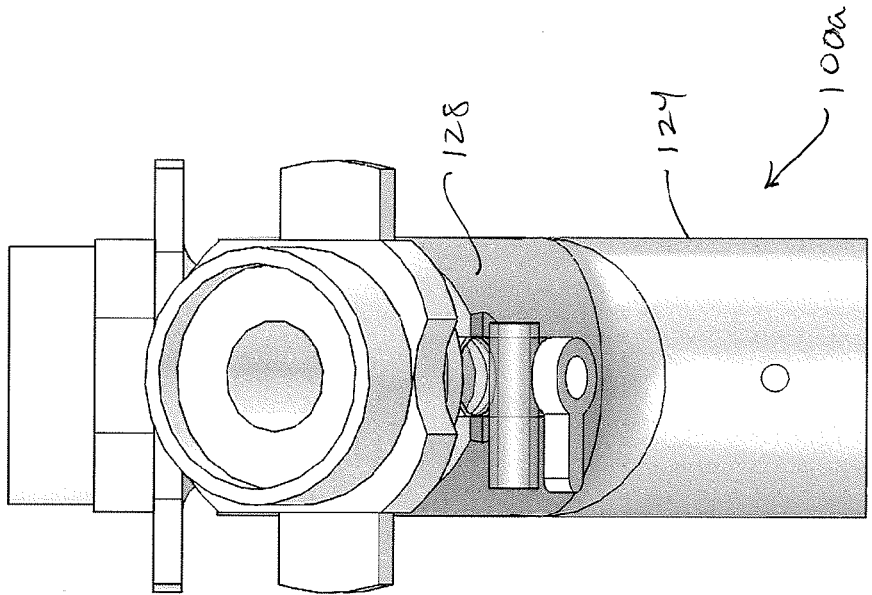
Figure 19:
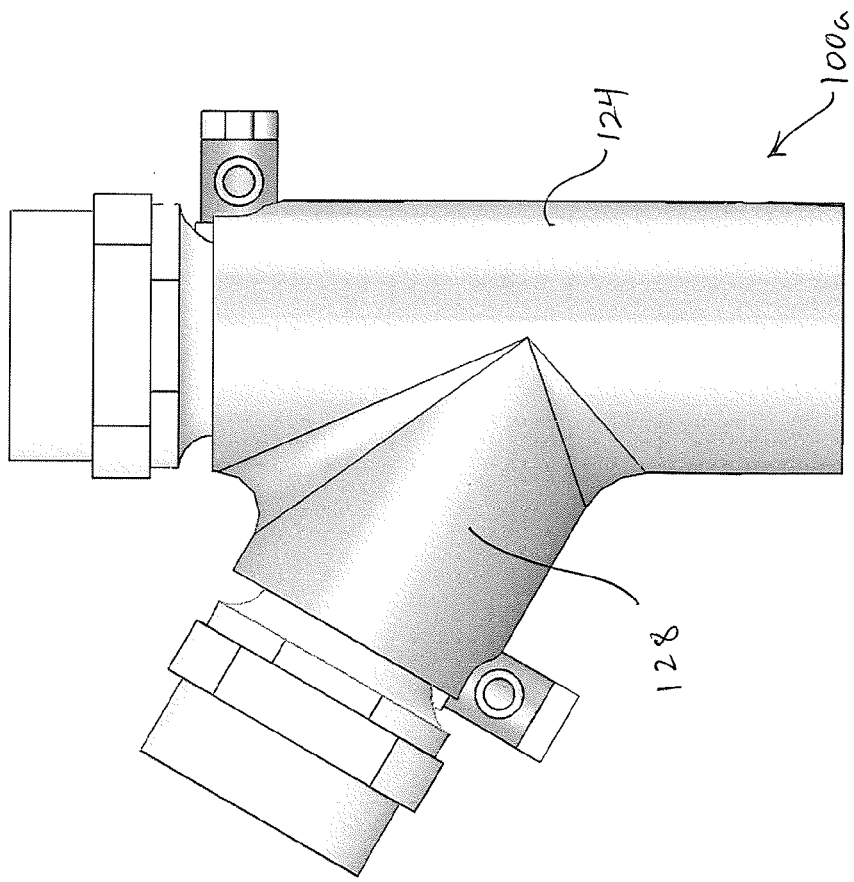
Figure 22:
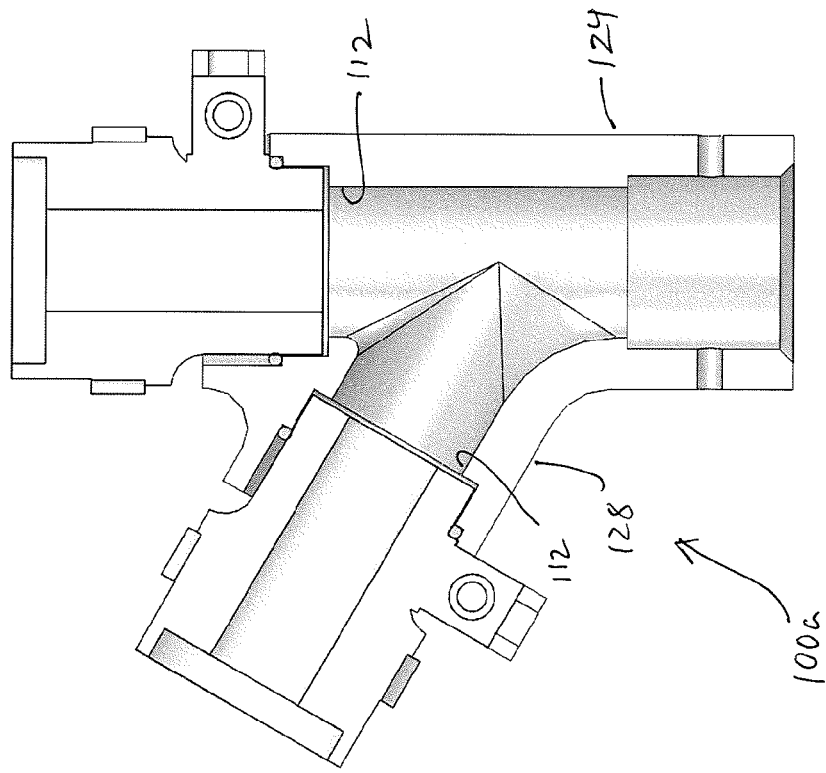
Figure 21:
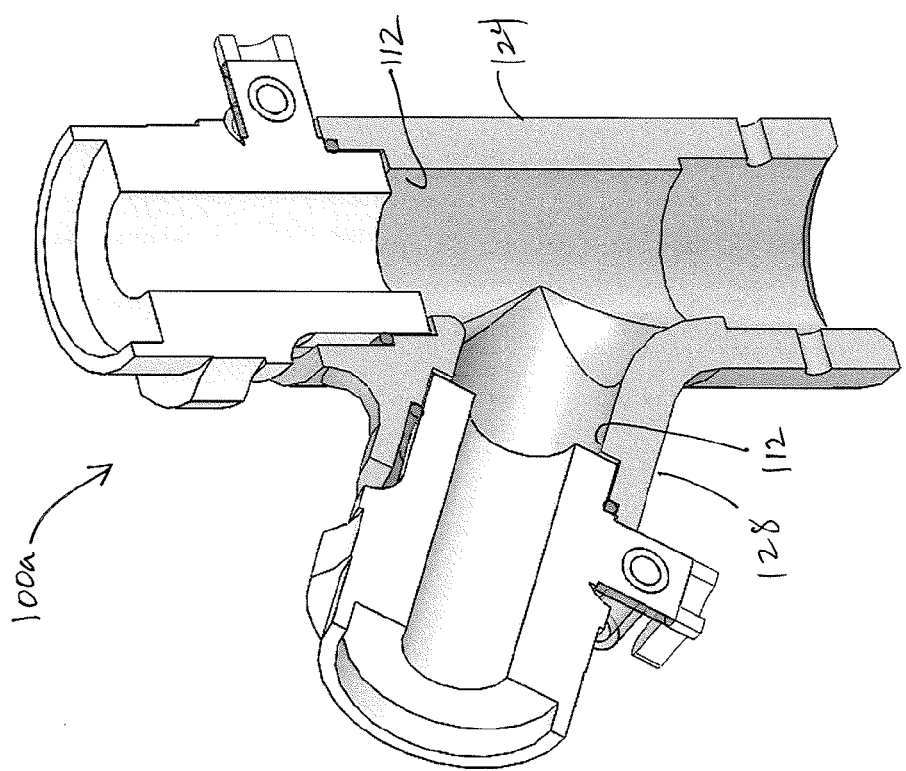
Figure 27:
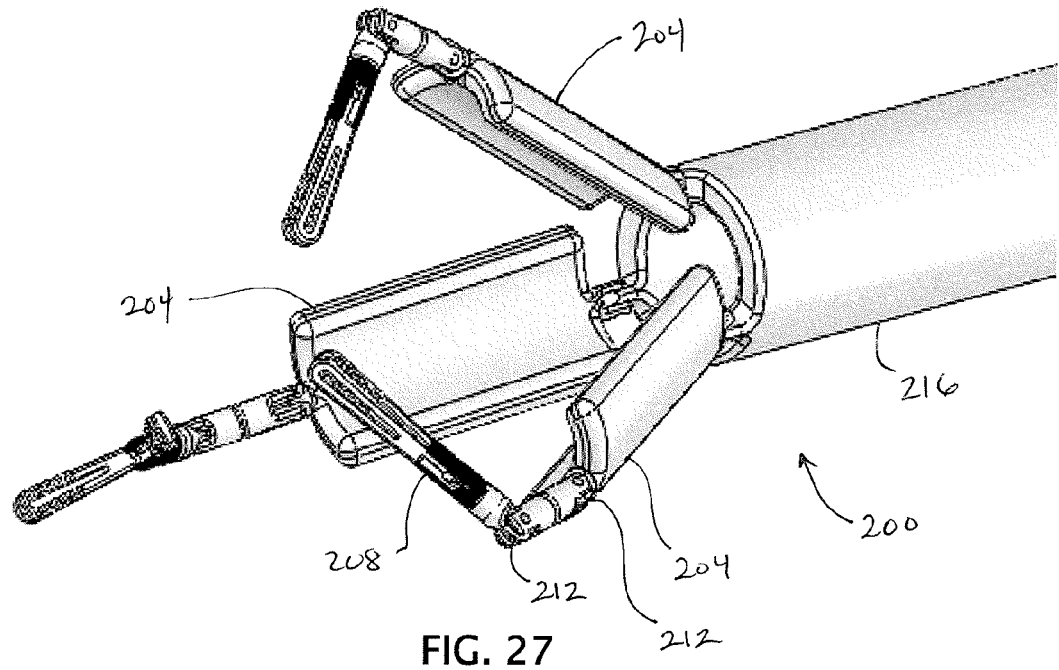
FIGS. 27-30 depict various views of one of the present one embodiment of the present devices having a set of multi-degree-of-freedom arms.
Figure 28:
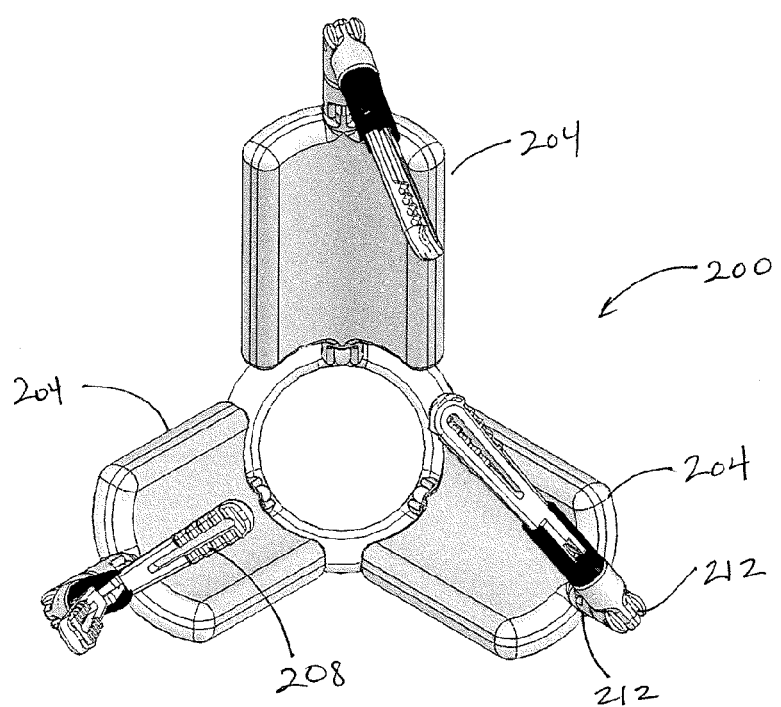

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as being largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, medical device, or apparatus that "comprises," "has," "includes" or "contains" one or more elements possesses those one or more elements, but is not limited to possessing only those one or more elements. Likewise, an element of a system, medical device, or apparatus that "comprises," "has," "includes" or "contains" one or more features possesses those one or more features, but is not limited to possessing only those one or more features. For example, a medical device that comprises a platform and a magnetically-attractive material includes the specified features but is not limited to having only those features. Such a medical device could also include, for example, a camera.

Further, a device or structure that is configured in a certain way is configured in at least that way, but it can also be configured in other ways than those specifically described.

Referring now to the drawings, and more particularly to FIGS. 1-8, shown there and designated by reference numeral 10 is one embodiment of the present medical devices that includes a magnetically attractive platform 14 and a multi-degree-of-freedom camera 18. More particularly, FIGS. 1-4 depict various views of device 10 in a deployed configuration, and FIGS. 5-8 depict various views of device 10 in a collapsed configuration.

In the embodiment shown, device 10 comprises a platform 14 comprising a magnetically-attractive material (e.g., magnetically-attractive members 22); and a camera 18 coupled to the platform and configured to be moved in at least three degrees of freedom relative to the platform, where the camera's movement in each respective degree of freedom is controlled by a separate actuator coupled to the platform. Device 10 may be positioned within a body cavity of a patient and magnetically coupled to a device located external to the patient. The external device may comprise complementary magnetically-attractive material that allows movement of the externally-located device, due the attractive force between the magnetically-attractive materials disposed on opposite sides of the body tissue bordering the cavity, to cause movement of device 10. Device 10 can be inserted or introduced into the relevant body cavity in any suitable fashion. For example, the device can be inserted into the cavity through a puncture (not shown) in the wall defining the cavity, through a tube or trocar extending into the cavity through a puncture or natural orifice, or may be inserted into another portion of the patient and moved into the cavity with the externally-located and magnetically-coupled device. If the cavity is pressurized, device 10 can be inserted or introduced into the cavity before or after the cavity is pressurized.

In the embodiment shown, device 10 further comprises: a housing 26 (e.g., a domed housing) disposed around at least a portion of camera 18, and housing 26 is at least partially (e.g., entirely) transparent. In the embodiment shown, substantially all of housing 26 that is viewable by camera 18 is substantially transparent. In the embodiment shown, device 10 further comprises a wiper arm 30 configured to move relative to housing 26 As used in this disclosure, "move relative to the housing" means that wiper arm 30 can move relative to platform 14 and/or housing 26 can move relative to platform 14, and/or one of housing 26 and wiper arm 30 can be fixed relative to platform 14, as long as there is relative movement between wiper arm 30 and housing 26.

Unlike conventional surgical imaging equipment (e.g., laparoscopic surgical imaging equipment), device 10 comprises camera 18 mounted on a MAGS platform 14 that allows it to enter through the same entry port as the other surgical tools, without blocking the entry port. While the physical manipulation of a conventional camera allows for control of pan, tilt and horizon correction by physically rotating the connection to the outside world, device 10 can be configured to motorize these functions with actuators on or in device 10 for remote (e.g., wireless) control such that some embodiments of device 10 can be tethered with only relatively simple power leads, which does not prevent other tools from being introduced. In this way, and in contrast to traditional endoscopes, embodiments of device 10 can be moved independent of the entry port.

In the embodiment shown, wiper arm 30 comprises a resilient wiper blade 34 (e.g., squeegee blade) coupled to wiper arm 30, and device 10 is configured such that wiper blade 34 contacts housing 26 such that if housing 26 moves relative to wiper arm 30, at least a portion of wiper blade 34 maintains contact with housing 26. In the embodiment shown, housing 26 is configured to rotate relative to platform 14 (e.g., to be rotated by a gear motor or any other suitable actuator relative to platform 14 and wiper arm 30), and wiper arm 30 is coupled in fixed relation to platform 14. In other embodiments, wiper arm 26 is configured to move relative to platform 14 and/or housing 26 is coupled in fixed relation to platform 14. In this way, wiper arm 30 and/or wiper blade 34 can wipe and/or clean housing 26 to remove material and/or reduce smudging.

Figure 48:
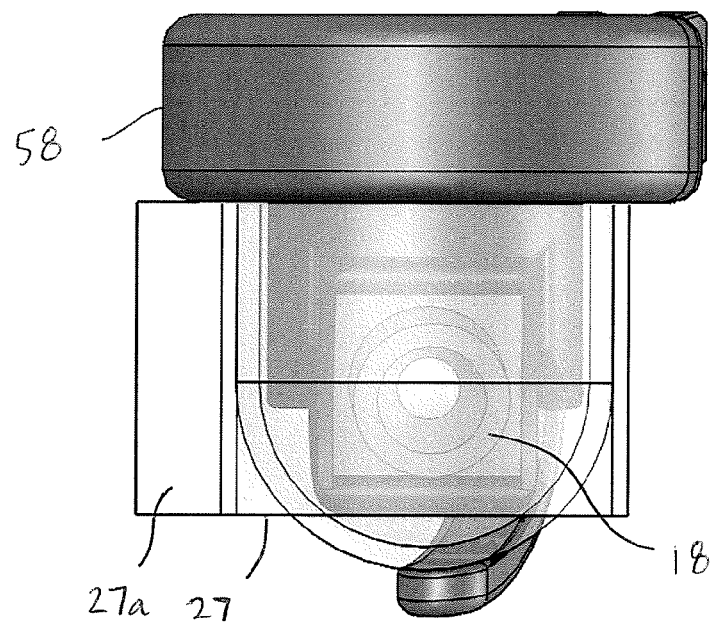
FIGS. 48 and 49 depict camera configurations that include removable/movable films that can be used to shield the camera from foreign material.
Figure 49:
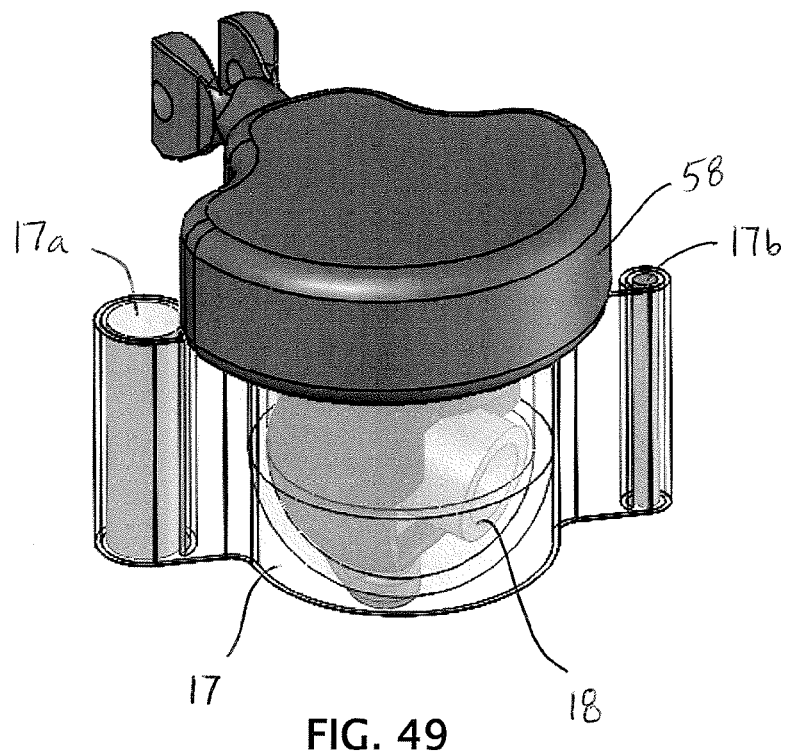

In other embodiments, device 10 is configured to "clean" housing 26 by removing a removable transparent film, or advancing an advanceable film when it becomes dirty or is otherwise in need of "cleaning." For example, housing 26 (e.g., a portion of housing 26) can be covered by a transparent film, such that if housing 26 becomes blocked due to foreign material, the film and/or a layer of the film can be removed by a grasper (e.g., a laparoscopic, endoscopic, and/or MAGS grasper) and peeled away. As shown in FIG. 48, such a film 27 could include a tab 27a that protrudes away from the camera and facilitates grasping of the film. In some embodiments, housing 26 is omitted, and a camera lens is covered with a transparent film (e.g., a film with an adhesive layer, like film 27, which could include tab 27a) such that the film can be removed in-vivo (e.g., when device 10 is disposed in a body cavity of a patient). In some embodiments (e.g., FIG. 49), film 17 lacking an adhesive (or that has a weak adhesive) can be disposed on an advanceable roll 17a on one side of housing 26 and coupled to a receiving roller 17b on another side of housing 26 such that the receiving roller can be rotated to advance film from the advanceable roll to the receiving roller to move a clean section of the film over the housing. All such films can be disposable and/or biodegradable. In some embodiments, such films can comprise a biocompatible material such that, if removed from the housing or the lens, can be simply "dropped" in the body cavity of the patient to be absorbed and disposed of by the natural processes of the patient's body.

Additionally, in the embodiment shown, platform 14 is configured such that if platform 14 is disposed in a body cavity of a patient, platform 14 can be percutaneously coupled to a power source and/or signal source external to the body cavity. For example, in the embodiment shown, platform 14 includes opening 38 to permit a power- and/or signal-delivery apparatus (e.g., needle, wire, or the like) to be inserted through the skin of a patient, and through opening 38, to conduct electricity to platform 14. Other embodiments can comprise any suitable number of openings 38 (e.g., one, two, three, or more). In the embodiment shown, device 10 also includes a conductive portion 42 facing a lower side 46 of device 10. In some embodiments, a conductive portion 42 is adjacent to each opening 38; in other embodiments, a conductive portion 42 can substantially surround each opening 38. Conductive portions 42 can each comprise any suitable material, such as, for example, silver, copper, silver-covered copper, or any other suitably conductive materials (e.g., metals, polymers).

In some embodiments, conductive portions 42 each includes a groove (e.g., having co-linear portions opposite sides of opening 38) configured to receive a portion (e.g., anchor) of a power- and/or signal-delivery apparatus, such as, for example, to resist rotation of the power- and/or signal-delivery apparatus relative to device 10 when the power- and/or signal-delivery apparatus is under tension. As a result of configuring device 10 in this manner, a power- and/or signal-delivery apparatus can pass through opening 38 and contact an adjacent conductive portion 42 such that electrical communication is enabled between the power- and/or signal-delivery apparatus and conductive portion 46. Device 10 can also be configured such that camera 18 is in electrical communication with conductive portion 42 using, for example, wires, conductive traces, or a direct connection, such that when a power- and/or signal-delivery apparatus is connected to a power supply current is permitted to flow and energize the camera. For example, some embodiments of device 10 comprise a circuit board (e.g., a printed circuit board or PCB) comprising conductive traces electrically coupling the camera 18 to conductive portions 42. Additionally, in the embodiment shown, device 10 includes an enlarged tapered portion 50 that, as shown, can have an inverted conical shape, at an upper end of each opening 38, to facilitate insertion of a power- and/or signal-delivery apparatus into the opening. Alternatively or additionally, in some embodiments, device 10 (e.g., platform 14) comprises a power source, such as a battery or the like. In some embodiments, body 54 can be configured for RF-induction from an external RF source and/or RF transmission for control and/or communication (e.g., between camera 18 and an external display).

In the embodiment shown, platform 14 comprises a body 54 and a camera arm 58 pivotally coupled to body 54; camera 18 is coupled to camera arm 58; and camera arm 58 is configured to be pivoted between a collapsed position (collapsed configuration shown in FIGS. 5-8) and a deployed position in which at least a portion of camera 18 is farther from body 54 than in the collapsed position (deployed configuration shown in FIGS. 1-4). In the embodiment shown, camera arm 58 is pivotally coupled to body 54 such that in the collapsed position, camera 18 is configured to face away from platform 14 (e.g., away from a longitudinal end 62 of body 54) and/or such that camera arm 58 is adjacent to or closer to longitudinal end 62 of body 54 than in the deployed position. In the embodiment shown, platform 14 comprises a hinge 66 pivotally coupling body 54 and camera arm 58. In this way, when camera arm 58 is in the collapsed position, camera 18 is substantially aligned with body 54 of platform 14 such that camera 18 can be used to provide "vision" during insertion and removal of device 10 from a patient, such as, for example, to improve safety and accuracy of insertion and removal. Examples of cameras suitable for use as camera 18 include CCIQ Mini Camera MO-S 1588-5D and MO-S1788-5D by Misumi Electronics Corp., Chung-Ho City, Taipei Shann, Taiwan, R.O.C.

In the embodiment shown, camera 18 is configured to be coupled to an external display (not shown) through wires 70 (or in other embodiments, a flex circuit) extending between camera 18 and body 54. In other embodiments, camera 18 is configured to be coupled to an external display through hinge 66. For example, in some embodiments, one or more wires 70 are enclosed in hinge 66 (e.g., to reduce the likelihood of the wires getting caught or broken during movement of the hinge). In other embodiments, hinge 66 comprises a slip-ring connector and/or a flex circuit. In some embodiments, a tether or the like couples to wires 70 and to an external display. In other embodiments, body 54 comprises a transceiver or other wireless communications module that couples wirelessly to an external monitor (e.g., via an external receiver coupled to an external monitor).

In the embodiment shown, when camera arm 58 is in the deployed position, a lens 74 of camera 18 is disposed below a lower surface (e.g., 46) of platform 14 (e.g., of body 54). In the embodiment shown, platform 14 (e.g., body 54) has two ends 62 and 78, and a longitudinal midpoint 82, and camera 18 is closer to end 62 than midpoint 82. In other embodiments, camera 14 can be coupled to platform 14 (e.g., body 54) such that camera 18 is nearer midpoint 82 than either end 62 or 78. In the embodiment shown, device 10 is configured such that camera 18 can be used to view a 360-degree field-of-view around platform 14 (e.g., around camera arm 58) without moving platform 14. In some embodiments, camera 18 coupled in fixed relation to platform 14 (e.g., camera arm 58) and a domed lens is provided to enable 360-degree field-of-view for the camera without moving the camera. In other embodiments, device 10 can comprise two cameras, such as, for example, one camera at each longitudinal end of body 54.

In the embodiment shown, camera 18 is configured to detect light in the visible spectrum. In some embodiments, camera 18 is configured to detect light in the infrared (IR) spectrum. In some embodiments, camera 18 is configured to detect light in all of the visible, IR, and ultraviolet (UV) spectra. In some embodiments, camera 18 comprises a plurality of cameras configured to detect light in all of (and/or a selected one or more of) the visible, IR, and UV spectra. For example, in some embodiments, camera 18 is configured for hyper-spectral imaging, such as, for example, to enable camera 18 to detect blood flow and/or perfusion. Certain of these spectra can also be useful to detect organs and the like on opposite sides of tissue being cut into (e.g., to alert a surgeon when a cut should be made elsewhere). In another example, certain of these spectra are useful for detecting certain medical and/or pharmacological dyes (e.g., for targeting tissue during tumor removal).

In some embodiments, camera 18 comprises a liquid lens that allows for zoom and/or focus by distorting a liquid rather than through the mechanical manipulation of optical lenses. Some embodiments of device 10 can be configured for actuated pan, tilt, horizon correction, zoom and focus. In some embodiments, device 10 (e.g., platform 14) comprises fiber-optic leads or light-emitting elements (e.g., light emitting diodes (LEDs) or incandescent light bulbs), for supplying light to assist or improve the function of camera 18 in the visible spectrum.

Some embodiments of the present multi-degree-of-freedom cameras for a medical procedure comprise device 10 and an apparatus for moving the platform within a body cavity of a patient when the apparatus is outside the body cavity, the apparatus comprising a magnetic assembly (e.g., configured to magnetically couple to magnetically-attractive members 22 of device 10) to move device 10 (e.g., platform 14) within the body cavity of a patient when the apparatus is outside the body.

Referring now to FIGS. 9-16, shown there and designated by the reference numeral 100 is one embodiment of the present branched connectors configured to be coupled to a surgical overtube. In the embodiment shown, branched connector 100 has an overtube connection 104 configured to be coupled to an overtube (and shown coupled to an overtube 108). In the embodiment shown, branched connector 100 also has at least two entry ports 112 that each includes at least one seal structure 116, with one of the seal structures being configured to accept and maintain a seal around a portion of an endoscope. In the embodiment shown, branched connector 100 is also configured to connect (e.g., via connection 120) to an insuflation device downstream of seal structure or seal structures 116 for a given entry port 112 for the introduction and maintenance of pneumoperitoneum. In the embodiment shown, branched connector 100 is configured with two connections 120 that each can be used to connect to an insuflation device. In the embodiment shown, branched connector 100 has a Y-shaped configuration.

Overtube connection 104 can be configured to be coupled to an overtube in various ways. For example, overtube connector 104 can be configured: to be adhered to an overtube; to be threaded (e.g., is provided with female threads) onto a correspondingly threaded overtube (e.g., that is provided with male threads); or to be press-fit onto an overtube (e.g., with an internal diameter slightly smaller than the external diameter of an overtube).

Some embodiments of branched connector 100 can be configured to permit staging, delivery, and/or removal of tools without leakage (e.g., while substantially preventing leakage) of pneumoperitoneum; provide a first pathway or channel to permit delivery of a tool (e.g., a MAGs tool), and a second channel to permit simultaneous delivery of a scope (e.g., an EGD); provide connections to a conventional insuflation device to allow for pneumoperitoneum; and/or permit stay sutures to be used with the overtube to hold the overtube at a desired location/depth.

In other embodiments, the "branches" need not be physical branch structures (e.g., tubes). For example, in some embodiments, overtube connection 104 includes an opening such that a tether can pass through the opening and be sandwiched or pinched between branched connector 100 and overtube 108.

Referring now to FIGS. 17-22, shown there and designated by the reference numeral 100a is another embodiment of the present branched connectors configured to be coupled to a surgical overtube. Branched connector 100a is substantially similar to branched connector 100, with the primary exception being that branched connector 100a includes a straight portion 124 associated with one of the entry ports 112, and a side branch portion 128 associated with the other entry port 112.

Referring now to FIGS. 23-26 shown there and designated by the reference numeral 100b is another embodiment of the present branched connectors configured to be coupled to a surgical overtube. Branched connector 100b is similar to branched connectors 100 and 100a, with two primary exceptions. First, branched connector 100b has more than two (in the embodiment shown, three) entry ports 112 that each includes at least one seal structure (not shown, but substantially similar to seal structures 116). Second, in the embodiment shown, overtube connection 104 includes one of a tab and a corresponding slot (in the embodiment shown, a slot or J-slot 132), and is configured to be coupled to an overtube 108a having the other of a tab and a corresponding slot (in the embodiment shown, a tab or pin 136) by inserting tab 136 into corresponding slot 132 and turning tab 136 relative to corresponding slot 132 (e.g., by turning or rotating branched connector 100b relative to overtube 108a).

Some embodiments of the present medical devices comprise an overtube (e.g., overtube 108, 108a, or any other overtube described in this disclosure). In some embodiments, the overtube is coupled to the overtube connection (e.g., overtube connection 104, 104a) of the branched connector. In some embodiments, the overtube is rigid.

Referring now to FIGS. 27-30, shown there and designated by the reference numeral 200 is one embodiment of the present devices having a set of multi-degree-of-freedom arms 204. In the embodiment shown, device 200 comprises a set of multiple (specifically, three) multi-degree-of-freedom arms 204 equipped with interchangeable tips 208. Other embodiments can comprises more or less than three arms 204. In the embodiment shown, each arm 204 includes at least two joints 212, each joint associated with an actuator, as described in more detail below. In the embodiment shown, the interchangeable tips 208 are configured to be actuatable in one or more degrees of freedom relative to an arm 204 to which the interchangeable tip is coupled. In the embodiment shown, at least one (e.g., all) of interchangeable tips 208 comprises a grasper. In some embodiments, at least one of interchangeable tips 208 comprises a camera. In other embodiments, at least one of interchangeable tips 208 comprises a cautery tool. In other embodiments, at least one interchangeable tips 208 can comprise a stapler and/or a clip applier.

Figure 29:
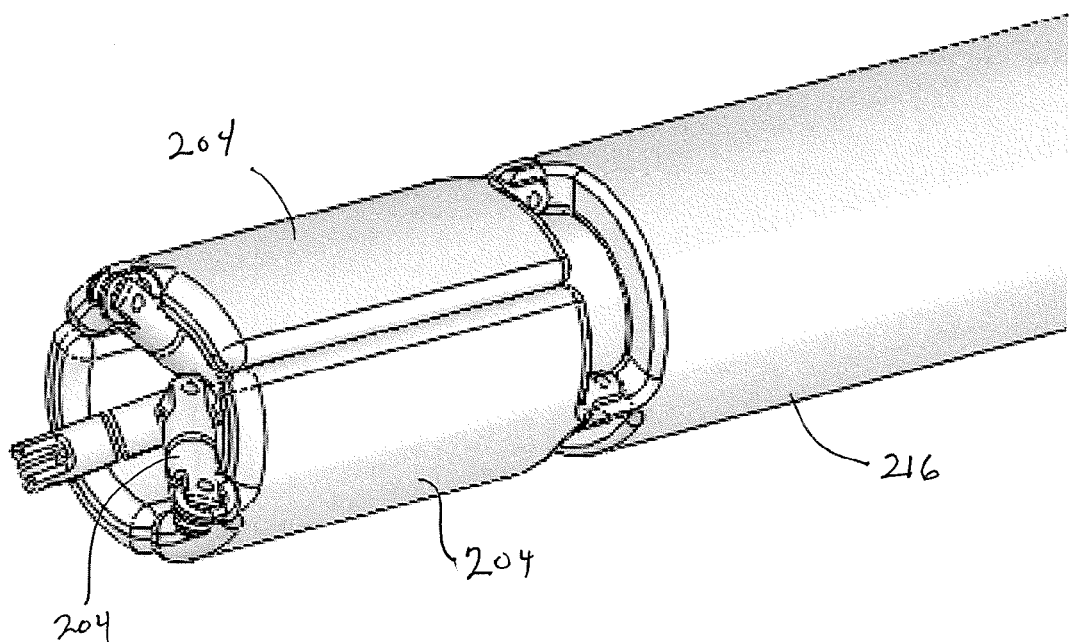
Figure 30:
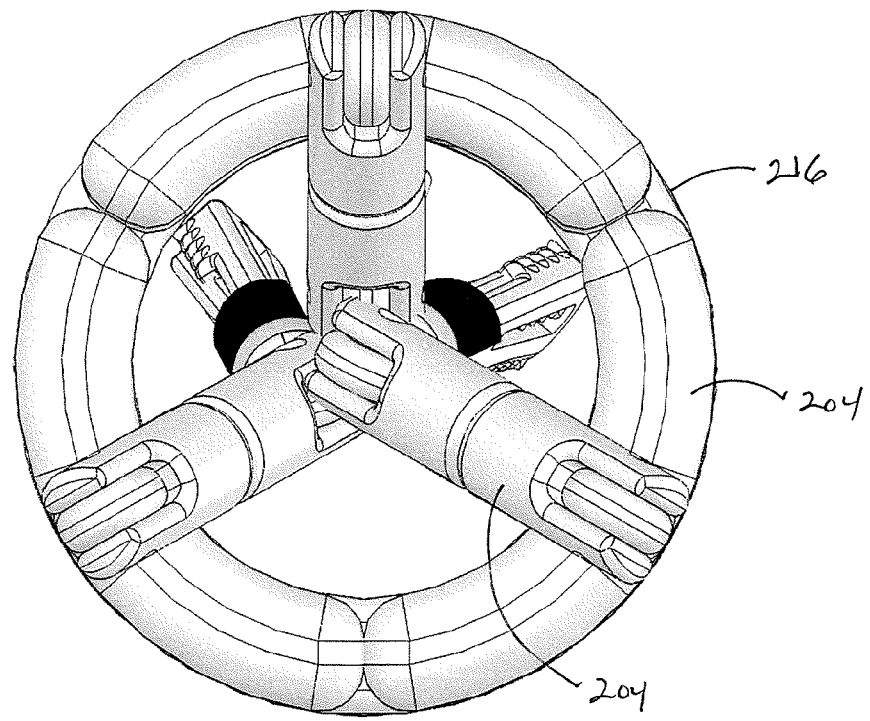

In the embodiment shown, the grasper (tip 208) is coupled to an arm configured such that the grasper is actuatable through an angular range of at least 90 degrees in at least one degree of freedom relative to the arm. In some embodiments, the grasper is coupled to an arm configured such that the grasper is actuatable through an angular range of at least 120 degrees in at least one degree of freedom relative to the arm. For example, in the embodiment shown, tip 208 is not limited to being in-line with a respective arm 204, and can have more degrees of freedom than are conventionally available (e.g., arm 204 can be extended past a target organ, and the grasper can be angled greater than 90 degrees relative to the arm to reach back and grasp tissue). In the embodiment shown, device 200 further comprises a rigid overtube 216 to which arms 204 are coupled. In other embodiments, overtube 216 can be configured such that arms 204 can be introduced through the overtube. FIGS. 29 and 30 depict device 200 in a collapsed configuration in which portions of arms 204 extend into overtube 216 such that arms 204 to not extend outward from the central longitudinal axis of overtube 216 beyond the outer perimeter (circumference) of overtube 216, such as, for example, for insertion and/or removal from a patient.

A given multi-DOF arm 204 (and any other multi-DOF arms described in this disclosure) may be used for one or more of several purposes—from organ retraction to electrocautery to stapling—depending on the tip that is used. In some embodiments, the tips are interchangeable. The arms (including tips) of a given set could be sterilized once for a procedure, and when a different tool is needed, the tip (e.g., the tool head) itself could be interchanged. The arms in a given set may be controlled ex-vivo by surgical staff, and, in certain applications, a majority of the arms of a given set would be located in-vivo.

The sections of a given multi-DOF arm 204 may be rigid, and may be sufficiently rigid that they do not flex or flex only minimally during a given procedure, to increase the likelihood that the surgeon will have adequate control and certainty of motion. As shown for example in FIGS. 44A and 44B, some embodiments of the arms include actuators housed in the arms. The effect of this may be to reduce the equipment located ex-vivo and allow for more motion due to the lack of mechanical interference.

Figure 31:
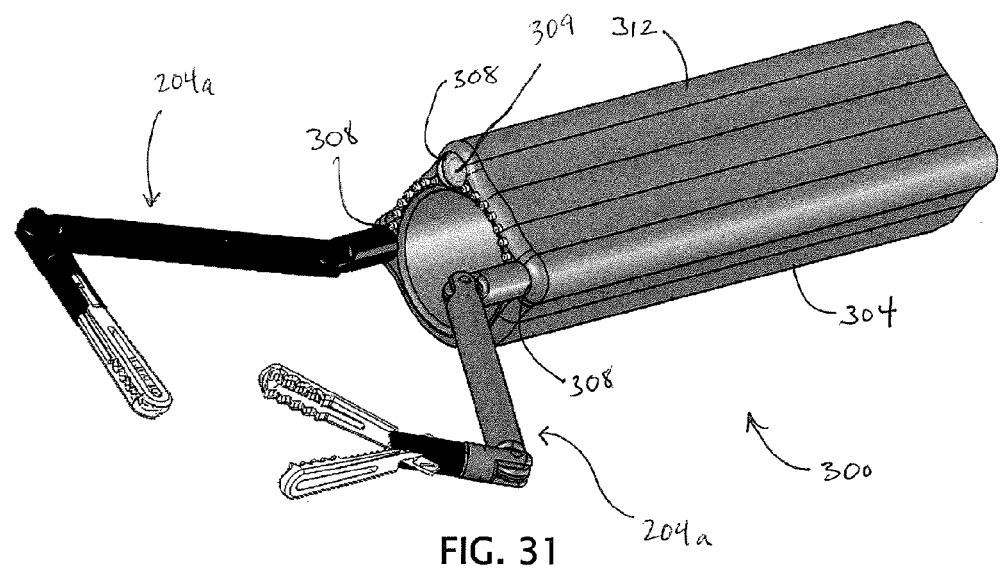
FIGS. 31-33 depict various views of one embodiment of the present medical devices comprising an overtube having peripheral channels in a wall of the overtube.
Figure 32:
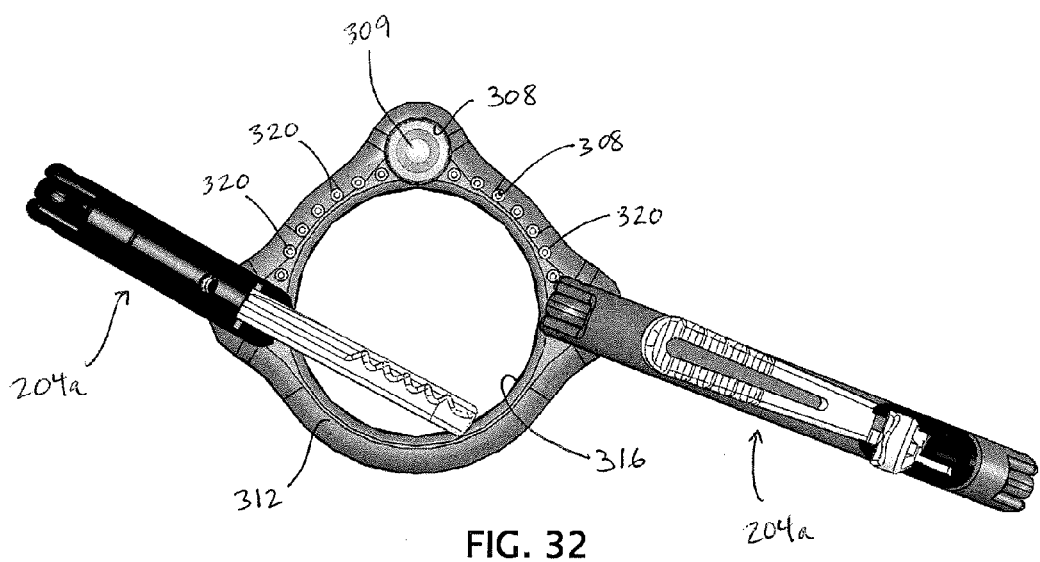
Figure 33:
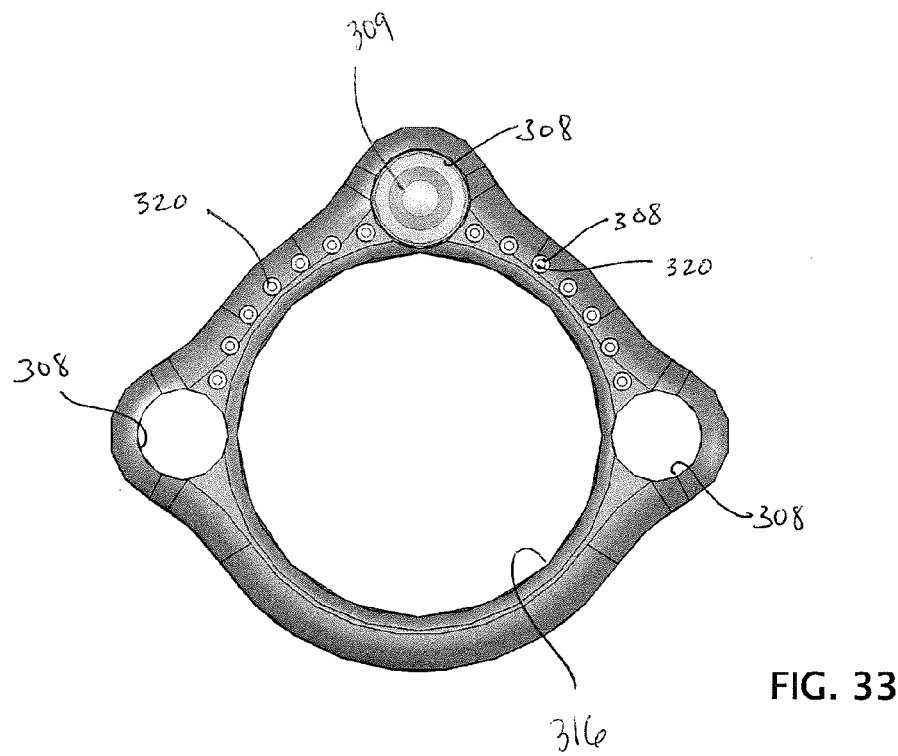
Figure 34:
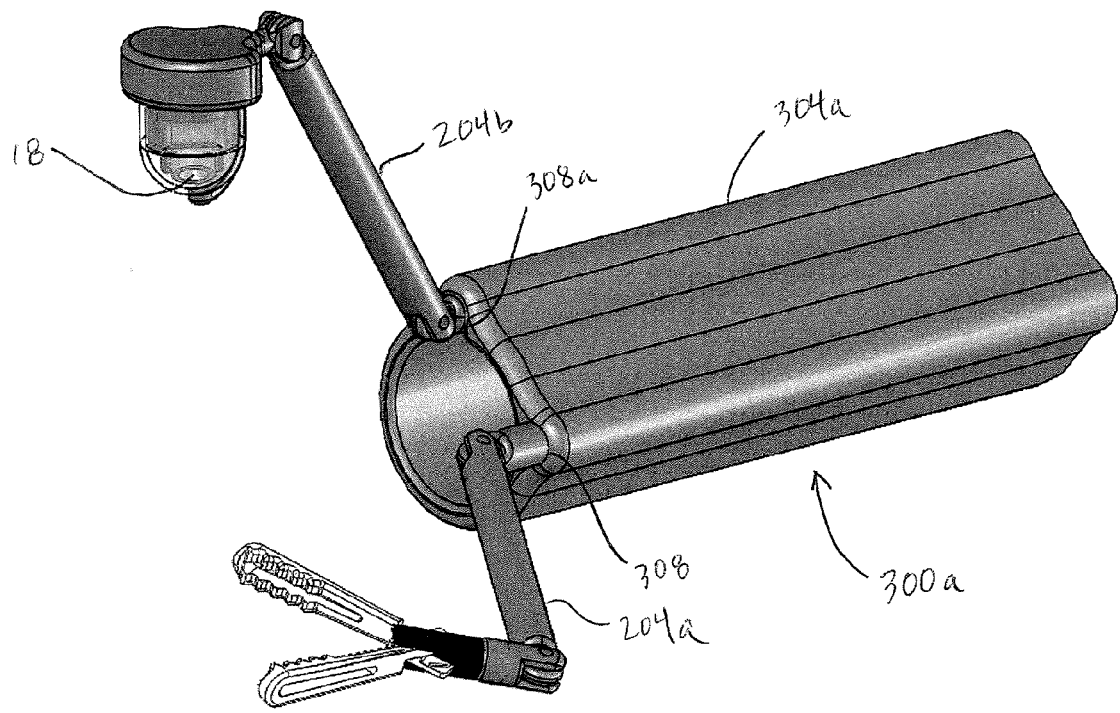
FIGS. 34-38 depict various views of another embodiment of the present medical devices comprising an overtube having at least one open peripheral channel in a wall of the overtube.
Figure 35:
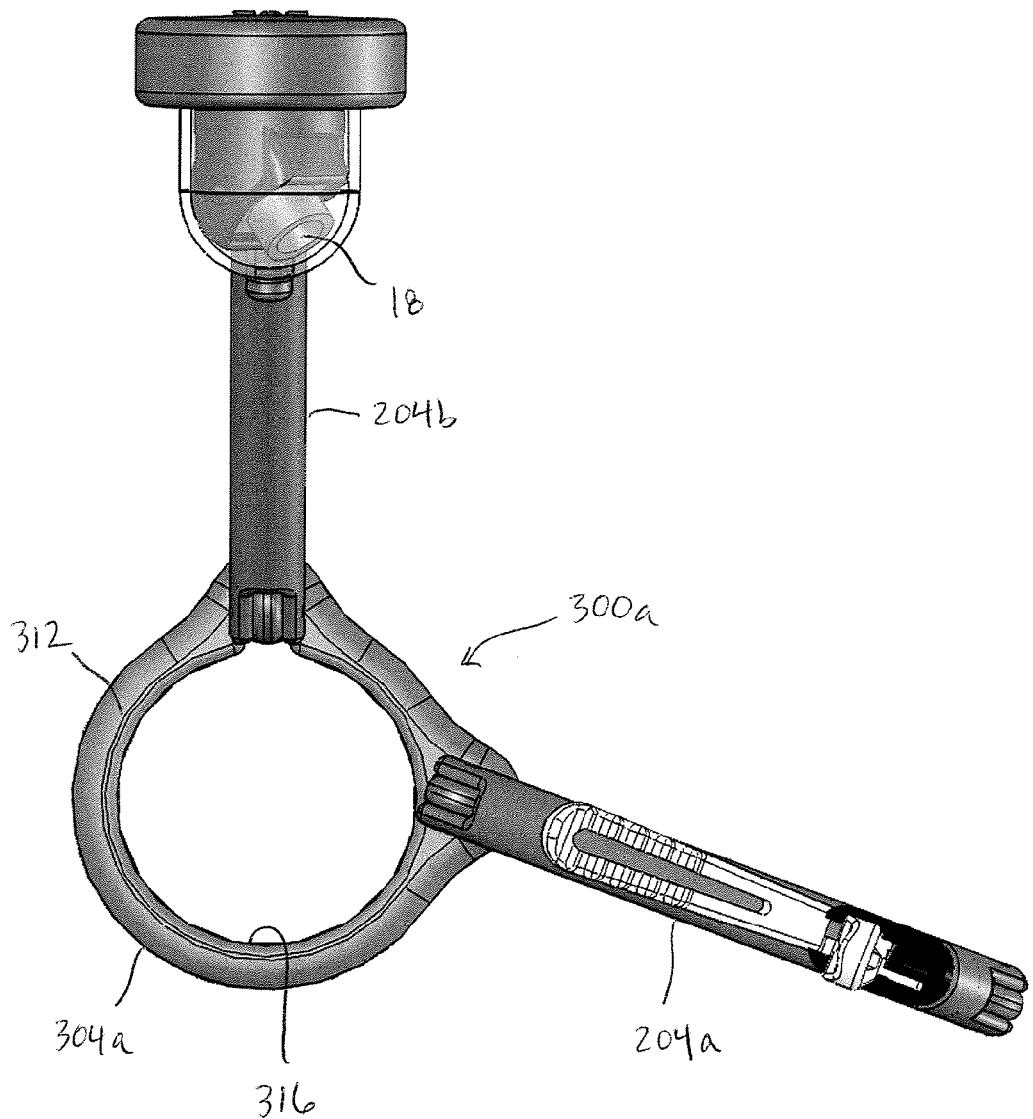
Figure 38:
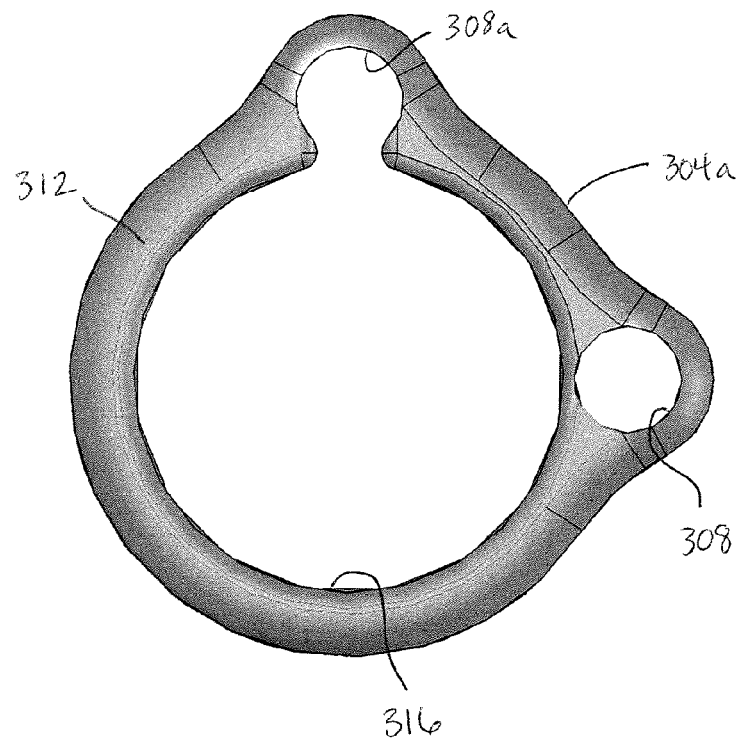

Referring now to FIGS. 31-33, shown there and designated by the reference numeral 300 is one embodiment of the present medical devices comprising an overtube 304 having peripheral channels 308 in a wall 312 of the overtube, which can be rigid. The channels 308 shown in these figures are closed (meaning they are bounded by wall 312), but in other embodiments on or more of them could be open (meaning not completely bounded by wall 312, an example of which is shown in FIG. 38). In the embodiment shown, overtube wall 312 defines a main lumen 316. Example sizes for the diameter of the main lumen (or otherwise the greatest dimension across the main lumen along a line perpendicular to the longitudinal axis of the lumen, in the case of non-cylindrical main lumens) range from 10-24 millimeters (mm), including 10 mm, 12 mm, 14 mm, 15 mm, 20 mm, and 24 mm. Other sizes can be used. In some embodiments, overtube 300 is rigid. In the embodiment shown, at least one of (e.g., a plurality of) channels 308 is configured to permit an optical fiber 320 to extend through the channel (e.g., to deliver light to a body cavity). Example sizes for the diameter of the channels 308 that are configured to house light-transmitting optical fibers 120 (or otherwise the greatest dimension across such a channel along a line perpendicular to the longitudinal axis of the channel, in the case of non-cylindrical such channels) range from 0.25 mm to 6 mm, including all sizes between these endpoints separated by 0.05 mm. Other sizes can be used. In some embodiments, at least one of the channels is configured to permit an optical fiber coupled to a camera 309 to extend through the channel; such a camera could provide an auxiliary/safety view, or potentially the primary view for a procedure. Camera 309 could serve the purpose of an EGD during insertion and/or allowing for main lumen 316 to be clear for other equipment. In some embodiments (e.g., those in which overtube 304 is rigid), at least one of (e.g., a plurality of) channels 308 is configured to permit a multi-DOF tool 204*a* to extend through the channel, which tool can be equipped with one of the interchangeable tips described above. An example size for the diameter of a channel 308 that is configured to house one of the present multi-DOF tools (or otherwise the greatest dimension across such a channel along a line perpendicular to the longitudinal axis of the channel, in the case of a non-cylindrical such channel) is 6 mm. Other sizes can be used. Tool 204*a* is similar to tool 204, except each link of tool 204*a* is configured to fit through channel 308, whereas the distal most link of tool 204 could not. In some such embodiments, device 300 comprises a set of multi-degree-of-freedom arms comprising three or more multi-degree-of-freedom arms.

In some embodiments, at least one of the channels 308 is configured to permit a tether to extend through the channel allowing for a power wire(s) and/or command/control wire(s) to run through the wall of the overtube. In some embodiments, overtube 304 is configured with a socket into which a tether supplying the power to a cautery tool could be plugged, and with another connector for a power supply. Such a socket and connector combination could be provided for any tool to be used during a procedure that requires power. This may help to reduce or eliminate leaks associated with a tether or tethers otherwise extending through the sealing structures described above.

In other embodiments, device 300 could include one or more RF antennas extending through one or more channels 308 of overtube 304, allowing for power to be conducted wirelessly from the overtube to a given device/tool, including, for example, a wireless camera and a cautery tool. In still other embodiments of device 300, one or more of the channels 308 could be used for suction (to remove fluid) and/or irrigation (to supply fluid) during a given procedure.

In other embodiments, overtube 304 comprises a flexible material, and is configured such that at least a portion of the overtube can be made substantially rigid by pressurizing the at least a portion of the overtube. In some embodiments, overtube 304 has a length, and is configured such that the overtube can be made substantially rigid along its length by pressurizing the at least a portion of the overtube. Fluid (e.g., air, saline, water, etc.) could be used to achieve such pressurization. In some embodiments of device 300, overtube 304 is configured with one or more chambers in wall 312 that allows for the overtube to pressured all at once or in sections. For example, for trans-vaginal work, overtube 304 could be pressurized to be rigid during insertion, but flexible in the relevant body cavity. As another example, overtube 304 could be flexible (not pressurized) during insertion, but one or more sections of it could made rigid (pressurized) in the relevant body cavity.

Some embodiments of device 300 comprise overtube 304 and any of the present branched connectors (e.g., 100, 100*a*, 100*b*). In some embodiments, the branched connector is coupled to overtube 304.

Figure 36:
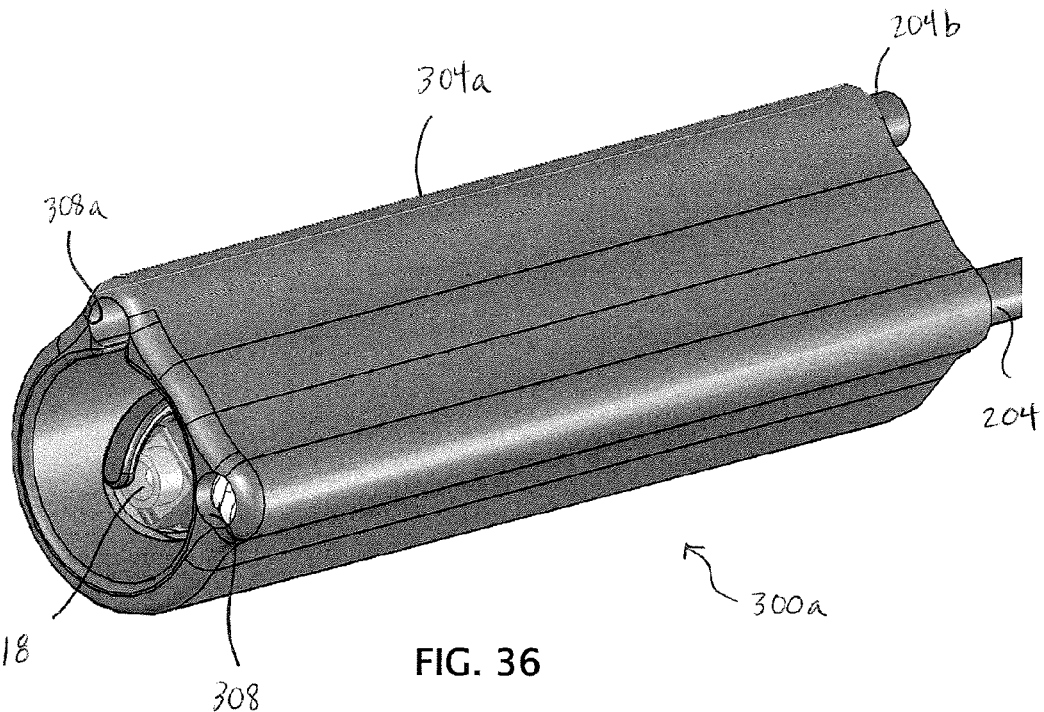
Figure 37:
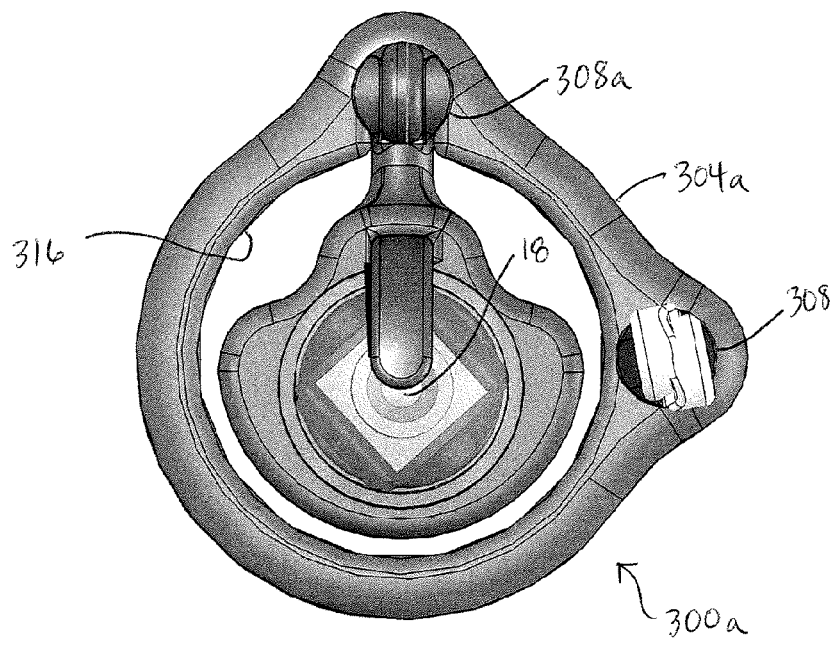

Referring now to FIGS. 34-38, shown there and designated by the reference numeral 300a is another embodiment of the present medical devices comprising an overtube 304a. Overtube 304a is similar to overtube 304 except that overtube 304a includes at least one open peripheral channel 308a in a wall 312 of the overtube. In the embodiment shown, a multi-DOF tool 204b that includes a camera 18 at its distal end occupies open peripheral channel 308a, and a multi-DOF arm 204a occupies closed channel 308. Camera 18 is coupled to the adjacent link in multi-DOF arm 204b through a joint that allows it to collapse into main lumen 316 as shown in FIGS. 36 and 37.

Figure 39:
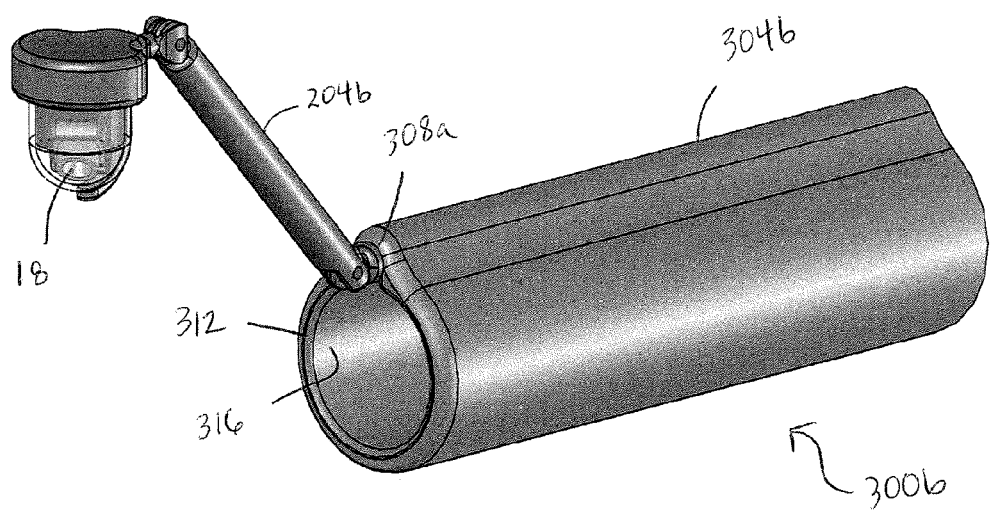
FIG. 39 depicts a perspective view of another embodiment of the present medical devices comprising an overtube having a single open peripheral channels in a wall of the overtube.

Referring now to FIG. 39, shown there and designated by the reference numeral 300b is another embodiment of the present medical devices comprising an overtube 304b, which is similar to overtubes 304 and 304a except that overtube 304b includes only a single open peripheral channel 308a in a wall of the overtube, which channel is occupied by a multi-DOF tool 204b that includes a camera 18 at its distal end.

Figure 40:
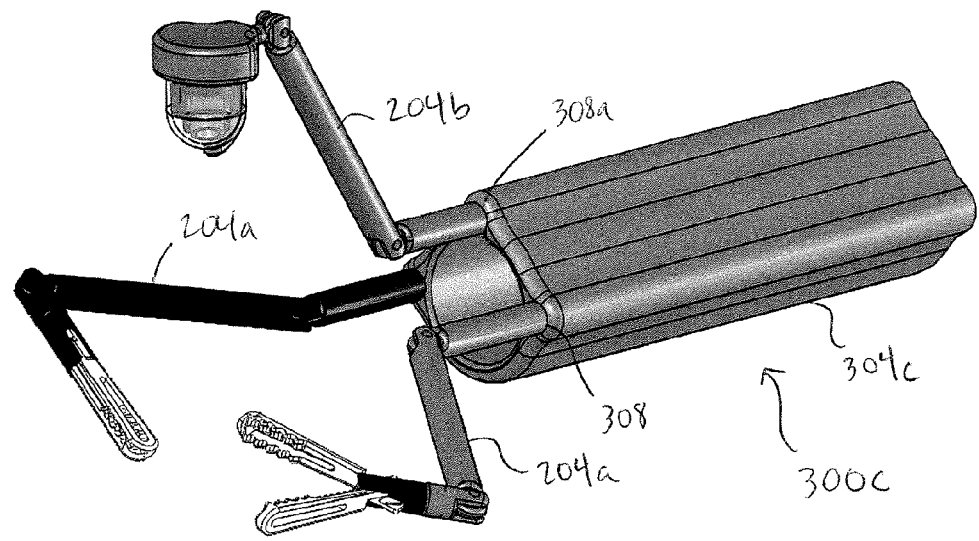
FIG. 40 depicts a perspective view of another embodiment of the present medical devices comprising an overtube.

Referring now to FIG. 40, shown there and designated by the reference numeral 300c is another embodiment of the present medical devices comprising an overtube 304c, which is similar to overtubes 304, 304a, and 304b except that overtube 304c includes an open peripheral channel 308a in a wall of the overtube, which channel is occupied by a multi-DOF tool 204b that includes a camera 18 at its distal end, and multiple (specifically, two) closed channels 308 that are occupied by multi-DOF arms 204a.

Overtubes 300, 300a, 300b, and 300c are examples of overtubes that may be rigid (not flexible and reinforced), and through which a flexible endoscope may be delivered to the operational theatre. Gross motion of the endoscope may be accomplished by moving the rigid overtube. Because these overtubes are configured with at least one peripheral channel through which an arm may be passed that can include a camera at its distal end, the surgeon may view some or all of the operational theatre with such a camera and not need the endoscope for that task. The endoscope and other tools may be delivered through embodiments of the present rigid overtubes without the relevant overtube kinking or collapsing.

Figure 41:
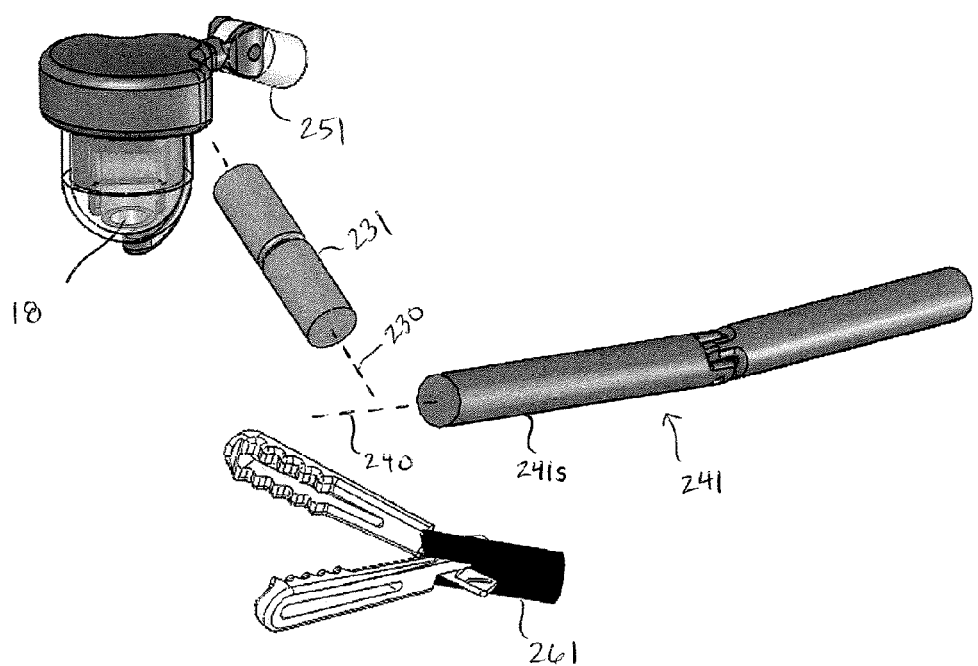
FIGS. 41-43 depict perspective views of embodiments of the links that can be used in the present multi-degree-of-freedom arms and different link combinations.
Figure 42:
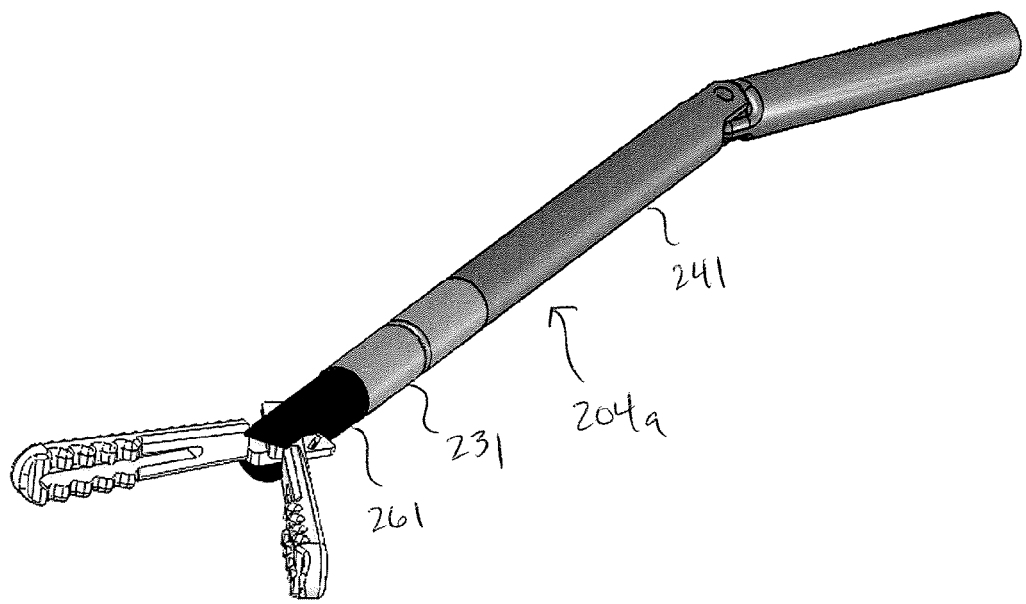
Figure 43:
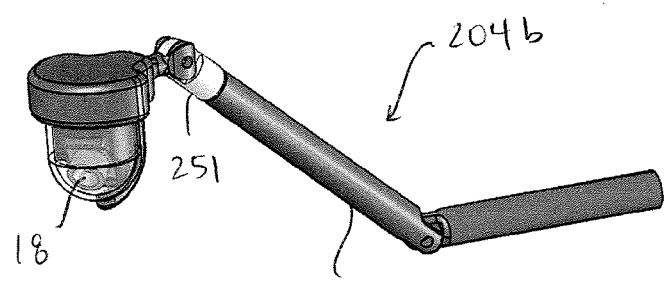

FIGS. 41-43 show examples of different links that can be used with the present multi-DOF arms and different link combinations. FIG. 41 shows a link 231 that has the ability to rotate about its axis 230, and a link 241 that has the ability to rotate perpendicular to the axis 240 of a given link segment 241s. FIG. 41 also shows camera 18 coupled to a link 251 that allows camera to rotate about the axis (not shown) of link 251, and graspers that include a link 261 configured to be coupled to any of the other links shown. FIG. 42 shows one example of a multi-DOF arm 204a, in which link 261 is coupled directly to link 231, which is coupled directly to link 241. FIG. 43 shows one example of a multi-DOF arm 204b, in which link 251 is coupled directly to link 241. In some embodiments, a link that is configured to telescope may be used with any of the present multi-DOF arms.

Any desired link combination may be used to generate the desired degrees of freedom for a particular multi-DOF arm having a particular tool. As a result, such tools (e.g., a camera, a cautery device, a stapler, a clip applier, etc.) could be configured, for example, to not being limited to axial motion (or motion that is in line with the straightened links of the arm). Some embodiments of the present multi-DOF arms are configured with a standardized connection to which a given tool (e.g., a camera, a cautery device, a stapler, a clip applier, etc.) would plug into.

Figure 44A:
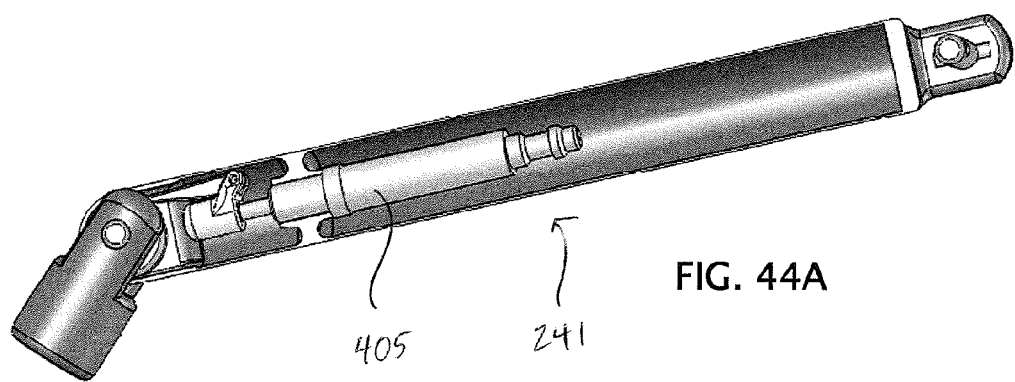
FIGS. 44A and 44B depict an embodiment of an actuator that can be used in embodiments of the present multi-degree-of-freedom arms to cause pivoting motion by one link segment about an axis that is perpendicular to the longitudinal axis of that link segment.
Figure 44B:
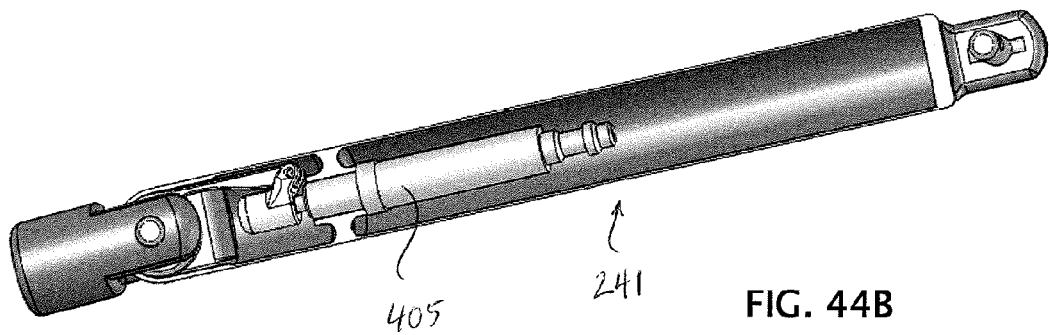
Figure 45A:
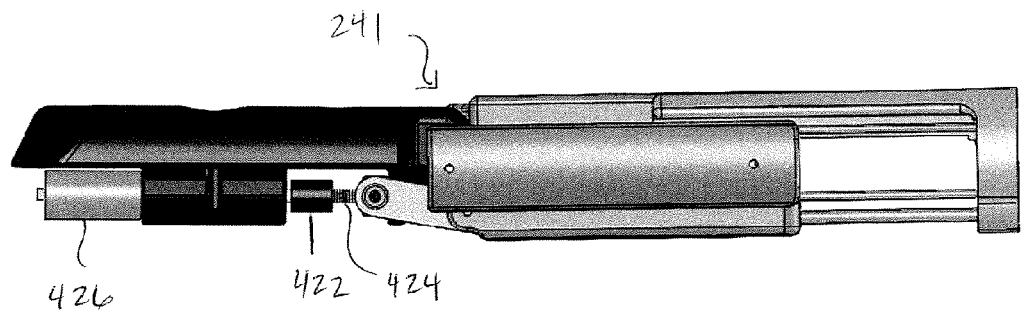
FIGS. 45A-45C depict an embodiment of an actuator that can be used in embodiments of the present multi-degree-of-freedom arms to cause the same motion as the actuator shown in FIGS. 44A and 44B.
Figure 45B:
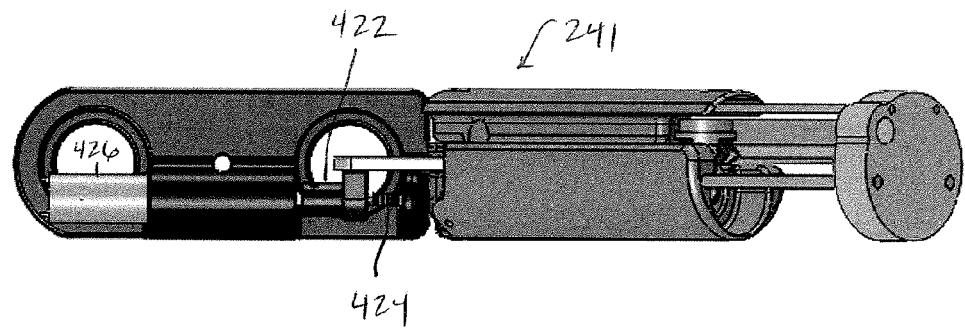
Figure 45C:
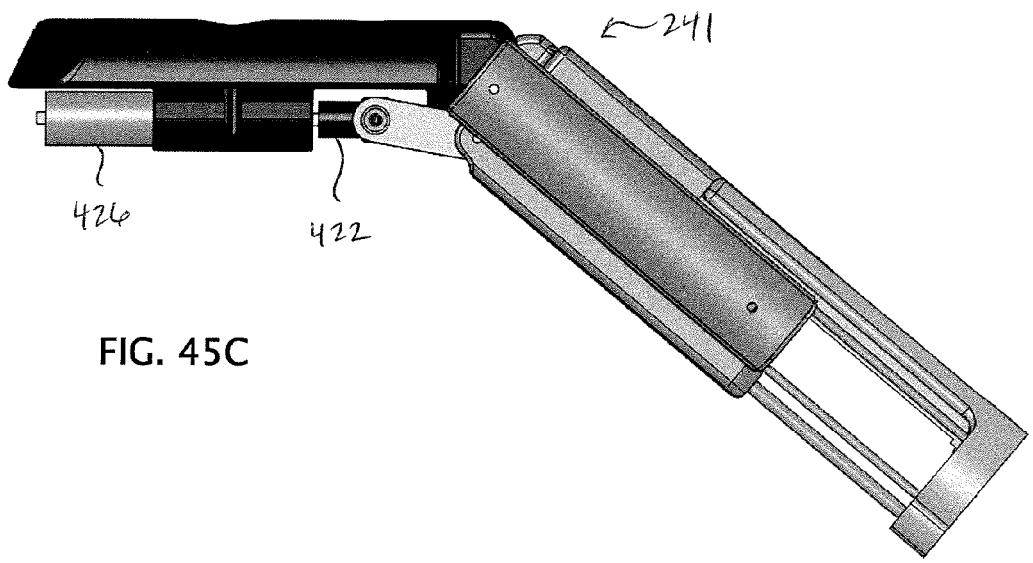
Figure 46:
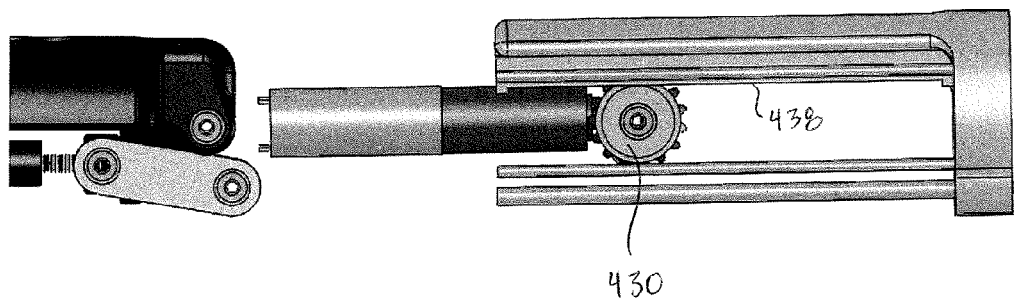
FIGS. 46 and 47 depict an embodiment of an actuator that can be used in embodiments of the present multi-degree-of-freedom arms to produce telescopic motion.
Figure 47:
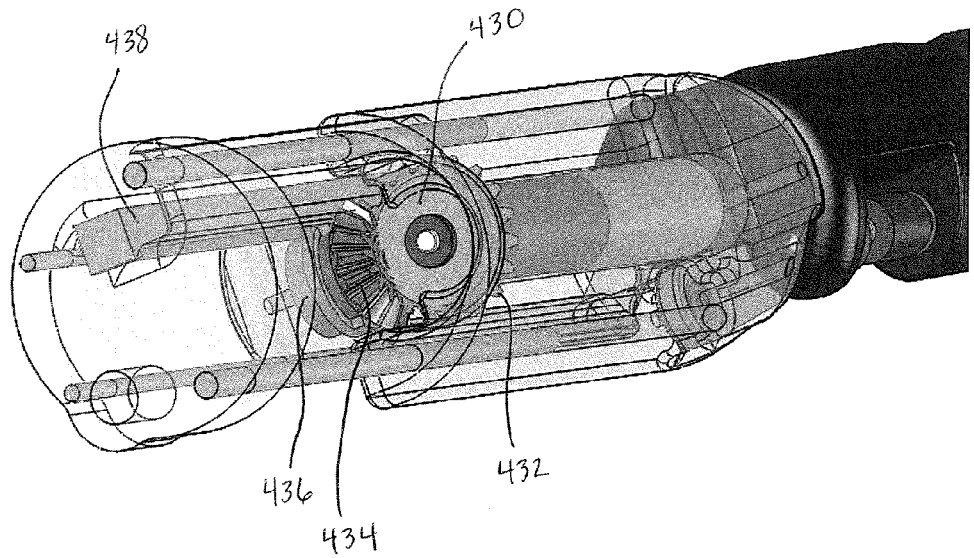

Embodiments of the present multi-DOF arms can be configured to be actuated by many different means. For example, and turning now to FIGS. 44A-47, shown there are examples of actuators that may be used to manipulate a given joint of one of the present multi-DOF arms. FIGS. 44A and 44B show an actuator that can be used to manipulate a joint that allows for rotation about an axis that is perpendicular to the axis of the link (e.g., of link 241) that houses the actuator. In particular, the actuator comprises a cylinder 405 that extends and retracts to cause such rotation/pivoting. The cylinder could be hydraulically-driven, for example. Another actuator that may achieve this motion is shown in FIGS. 45A-45C, where the traveler or hub 422 moves back and forth on a screw 424 that is driven by a motor 426 to convert rotational motion of the motor into linear motion of the hub and pivotal joint motion (and thus pivotal motion of the arm). FIGS. 46 and 47 show an actuator that can produce telescopic motion at a joint. In particular, as the gear 432 on motor 430 rotates, it rotates a second gear 434, which rotates a pinion 436, that drives a rack 438 linearly. As an alternative example, telescopic motion could be achieved with a screw drive or a cylinder. Rotational motion of a link such as link 230 could be achieved with a motor and hub.

The various illustrative embodiments of systems, apparatuses, devices, and methods described herein are not intended to be limited to the particular forms disclosed. Rather, they include all modifications and alternatives falling within the scope of the claims. For example, in some embodiments, the motors, hydraulic cylinders, and/or other actuators can be substituted with, and/or supplemented by, one or more manual drives (e.g., a pull string or manual screw drive to advance and/or withdraw the arm and/or tip, a knob or the like configured to rotate a threaded rod in the arm such that a nut or the like coupled to the threaded rod can be linearly advanced and/or withdrawn by rotating the knob, and/or a knob configured to rotate the tip itself); one or more torsion springs configured to bias and/or hold the arm in a biased direction relative to the platform (e.g., collapsed or deployed); one or more linear compression springs configured to bias or hold the arm in a biased direction relative to the platform (e.g., configured to bias the arm open relative to the body such that when the arm is released the spring will deploy the arm to a deployed or open position relative to the platform); one or more fluid actuators (e.g., hydraulic cylinders, bladders, fluidic muscles such as tubes that will retract or extend with pressure, bellows, and/or fluidic rotary actuators such as those that can convert rotary motion to linear motion); and/or one or more electric or electromagnetic actuators (e.g., linear voice coils, piezoelectric actuators, rotary or gear motors such as those in which rotary motion is converted to linear motion, linear actuators, shape-memory alloys such as nickel-titanium (e.g., nitinol), and/or electro-active polymers that can be configured to change shape in the presence of an electrical field. Examples of piezoelectric actuators include: what may be known in the art as a "squiggle" in which a screw or bolt is vibrated through a nut; what may be known in the art as a "finger" that "flicks" or impacts a ceramic surface to cause motion; and/or the like. In one example of any embodiment of the present devices using shape-memory alloys and/or electro-active polymers, alternate embodiments can comprise a shape memory alloy and/or electro-active polymer in place of any other actuator, such that the shape memory alloy and/or electro-active polymer can be configured to shorten and/or lengthen with the application of a voltage and/or current such that the arm can be deployed and/or collapsed. A version of shape-memory alloy nitinol (FLEXINOL is one trade name) that typically shrinks when heated may be used. Any of the various actuators can be incorporated into any of the various embodiments of the present devices, such as, for example, to actuate an arm and/or a tip or cameral relative to an arm. Some embodiments of the present multi-DOF arms and the camera of device 10 can be configured with actuators that operate in slave fashion to a master device (e.g., through one or more hand or foot controllers) that is manipulated remotely, and thus can be characterized as configured for robotic actuation.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A medical device comprising: a platform comprising a magnetically-attractive material, the platform comprising
    an elongated body and a camera arm; and
    a camera coupled to the camera arm of the platform and configured to be moved in at least three degrees of freedom relative to the platform, where the camera's movement in each respective degree of freedom is controlled by a separate actuator coupled to the platform;
    where the camera comprising;
        a housing disposed around at least a portion of the camera, the housing being at least partially transparent; and
        a wiper arm configured to move relative to the housing;
        where the wiper arm comprises a resilient wiper blade coupled to the wiper arm, and where the medical device is configured such that the wiper blade contacts the housing such that if the housing moves relative to the wiper arm, at least a portion of the wiper blade maintains contact with the housing;
    where the camera arm is pivotally coupled to an end of the elongated body such that, in a first one of the at least three degrees of freedom, the camera arm can pivot relative to the platform between a first position in which the camera arm is aligned with a longitudinal axis of the platform and a second position in which the camera arm is offset relative to the axis; and
    where, in a second one of the at least three degrees of freedom, the camera can move relative to the camera arm.

2. The medical device of claim 1, where the wiper arm is configured to move relative to the platform.

3. The medical device of claim 2, where the housing is coupled in fixed relation to the platform.

4. The medical device of claim 2, where the housing is configured to rotate relative to the platform.

5. The medical device of claim 1, where the housing is configured to rotate relative to the platform.

6. The medical device of claim 5, where the wiper arm is coupled in fixed relation to the platform.

7. The medical device of claim 1, where the platform is configured such that if the platform is disposed in a body cavity of a patient, the platform can be percutaneously coupled to a power source external to the body cavity.

8. The medical device of claim 1, where the platform comprises a power source.

9. The medical device of claim 1, where the platform comprises a body and a camera arm pivotally coupled to the body, the camera is coupled to the camera arm, and the camera arm is configured to be pivoted between a collapsed position and a deployed position.

10. The medical device of claim 1, where the platform includes an upper surface configured to contact an interior surface of a patient during use, and a lower surface opposite the upper surface, and the camera has a lens disposed below the lower surface of the platform.

11. The medical device of claim 1, where the platform has two ends and a longitudinal midpoint, and the camera is coupled to the platform such that the camera is nearer the midpoint than either end.

12. The medical device of claim 1, where the device is configured such that the camera can be used to view a 360-degree field-of-view around the platform without moving the platform.

* * * * *